(12) United States Patent
Hair et al.

(10) Patent No.: US 7,825,228 B2
(45) Date of Patent: *Nov. 2, 2010

(54) BONE MINERALIZATION PROTEINS, DNA, VECTORS, EXPRESSION SYSTEMS

(75) Inventors: Gregory A. Hair, Atlanta, GA (US); Scott D. Boden, Atlanta, GA (US)

(73) Assignee: Emory University

( * ) Notice: Subject to any disclaimer, the term of this patent is extended or adjusted under 35 U.S.C. 154(b) by 310 days.

This patent is subject to a terminal disclaimer.

(21) Appl. No.: 10/951,236

(22) Filed: Sep. 27, 2004

(65) Prior Publication Data

US 2006/0019392 A1 Jan. 26, 2006

Related U.S. Application Data

(60) Continuation of application No. 09/986,625, filed on Nov. 9, 2001, now Pat. No. 6,858,431, and a continuation of application No. 10/946,268, filed on Sep. 21, 2004, now abandoned, which is a continuation of application No. 09/986,625, filed on Nov. 9, 2001, now Pat. No. 6,858,431, which is a division of application No. 09/721,975, filed on Nov. 27, 2000, now Pat. No. 6,444,803, which is a continuation of application No. 09/124,238, filed on Jul. 29, 1998, now Pat. No. 6,300,127.

(60) Provisional application No. 60/054,219, filed on Jul. 30, 1997, provisional application No. 60/080,407, filed on Apr. 2, 1998.

(51) Int. Cl.
| | |
|---|---|
| C07H 21/02 | (2006.01) |
| C07H 21/04 | (2006.01) |
| C12Q 1/68 | (2006.01) |
| C12N 15/00 | (2006.01) |
| G01N 33/53 | (2006.01) |

(52) U.S. Cl. .................. 536/23.1; 435/6; 435/320.1
(58) Field of Classification Search .................. None
See application file for complete search history.

(56) References Cited

U.S. PATENT DOCUMENTS

| 4,800,159 | A | 1/1989 | Mullis et al. |
| 5,504,192 | A | 4/1996 | Gill et al. |
| 5,580,775 | A | 12/1996 | Fremeau, Jr. et al. |
| 6,858,431 | B2 | 2/2005 | Hair et al. |

FOREIGN PATENT DOCUMENTS

WO  WO 99/06563  *  2/1999

OTHER PUBLICATIONS

GenBank Accession No. AA205339, Jan. 27, 1997.*
Villareal, X.C. et al., Biochemistry, vol. 28, pp. 6483-6491 (1989).*
Silverman J.A. et al., PNAS USA, vol. 98, pp. 3092-3097 (2001).*
Zhu, H. et al., J. Biol. Chem., vol. 280, pp. 12137-12144 (2005).*
Graether, S. P. et al., Proteins, vol. 63, pp. 603-610 (2006).*
GenBank Accession No. AAA60993, Osteonectin, (May 1994).*
Cheng, Di et al., Growth Factors, vol. 22, pp. 233-241 (2004).*
Jung, J-W. et al., J. Biochem. Mol. Biol., vol. 37, pp. 28-34 (2004).*
Zhang, Y., Current Opinion Struct. Biol., vol. 18, pp. 342-348 (2008).*
B.L. Hogan, "Bone morphogenetic proteins: multifunctional regulators of vertebrate development," *Genes & Develop.*, 10:1580 (1996).
D.M. Kingsley, "What do BMPs do in mammals? Clues from the mouse *short ear* mutation," *Trends Genet.*, 10:16 (1994).
Boden, et al., "Differential effects and glucocorticoid potentiation of bone morphogenetic protein action during rat osteoblast differentiation in vitro," *Endocrinology*, 137:3401-3407 (1996).
Boden, et al., "Glucocorticoid-induced differentiation of fetal rat calvarial osteoblasts is mediated by bone morphogenetic protein-6," *Endocrinology*, 138:2820-28 (1997).
Alden, et al., *Neurosurgical Focus*, (1998).
Baumgartner, et al., "Constitutive Expression of phVEGF$_{165}$ After Intramuscular Gene Transfer Promotes Collateral Vessel Development in Patients With Critical Limb Ischemia," *Circulation*, 97(12):114-23 (1998).
Sambrook, et al., *Molecular Coloning: A Laboratory Manual*, Cold Spring Harbor Press, 2$^{nd}$ Edition (1988).
Davis, et al., *Basic Methods in Molecular Biology*, Elsevier (1986).
Ausubel, et al., *Current Protocols in Molecular Biology*, Wiley Interscience (1988).
Graham and Van Der, *Virology*, 52:456 (1973).
Kimura, et al., *Virology*, 49:394 (1972).
Sompayrac, et al., *Proc. Natl. Acad. Sci., USA*, 78:7575 (1981).
Potter, *Proc. Natl. Acad. Sci. USA*, 81:7161 (1984).

(Continued)

*Primary Examiner*—Teresa E Strzelecka

(57) ABSTRACT

The present invention is directed to isolated nucleic acid molecules that encode LIM mineralization protein, or LMP. The invention further provides vectors comprising nucleotide sequences that encode LMP, as well as host cells comprising those vectors. Moreover, the present invention relates to methods of inducing bone formation by transfecting osteogenic precursor cells with an isolated nucleic acid molecule comprising a nucleotide sequence encoding LIM mineralization protein. The transfection may occur ex vivo or in vivo by direct injection of virus or naked plasmid DNA. In a particular embodiment, the invention provides a method of fusing a spine by transfecting osteogenic precursor cells with an isolated nucleic acid molecule having a nucleotide sequence encoding LIM mineralization protein, admixing the transfected osteogenic precursor cells with a matrix and contacting the matrix with the spine. Finally, the invention relates to methods for inducing systemic bone formation by stable transfection of host cells with the vectors of the invention.

22 Claims, No Drawings

OTHER PUBLICATIONS

Sandri-Goddin, et al., *Molec. Cell Biol.*, 1:743 (1981).
Southern, E.M., *J. Mol. Biol.*, 98:503 (1975).
Sambrook, et al., *Molecular Cloning: A Laboratory Manual*, 2nd Edition, Ch/pp. 7.19-7.50, Cold Spring Harbor Press (1989).
Ausubel, et al., *Current Protocols in Molecular Biology*, John Wiley and Sons (1987).
Kohler and Milstein, *Nature*, 256:495-97 (1975).
MacPherson, "Soft Agar Techniques," *In Tissue Culture Methods and Applications*, Kruse and Paterson (eds), Academic Press (1973).
Harlow, et al., *Antibodies: A Laboratory Manual*, Cold Spring Laboratory (1988).
Nanes, et al., *Endocrinology*, 127:588 (1990).
Conner, et al., *Proc. Natl. Acad. Sci. USA*, 88:278 (1983).
D.V. Huntsberger, "The Analysis of Variance," *In Elements of Statistical Variance*, P. Billingsley (ed), pp. 298-330, Allyn & Bacon Inc., Boston, MA (1977).
Sigmastat, *Jandel Scientific*, Corte Madera, CA.
England, et al., *Biochim. Biophys. Acta*, 623:171 (1980).
Timmer, et al., *J. Biol. Chem.*, 268:24863 (1993).
Hair et al., *Leukemia Research*, 20:1 (1996).
Towbin, et al., *Proc. Natl. Acad. Sci. USA*, 76:4350 (1979).
Ausubel, et al., "Quantitation of rare DNAs by the polymerase chain reaction," *In Current Protocols in Molecular Biology*, Ch. 15, pp. 31-41, Wiley & Sons, Trenton, NJ (1990).
Chenchik, et al., *Clontechniques*, X:5 (1995).
Borson, et al., *PC Methods Applic.*, 2:144 (1993).
Gubler, et al., *Gene*, 25:263 (1983).
Liu, Y., et al., "BMP6 induces a novel LIM protein involved in bone mineralization and osteocalcin secretion," *Journal of Bone and Mineral Research*, 12:49 (1997).
Shawlot, W. and Behringer, R., "Requirement for Lim1 in head-organizer function," *Nature*, 374:425-430 (1995).
De Robertis, E.M., "Dismantling the organizer," *Nature*, 374:407-408 (1995).

\* cited by examiner

SEQUENCE LISTING

<160> NUMBER OF SEQ ID NOS: 35

<210> SEQ ID NO 1
<211> LENGTH: 457
<212> TYPE: PRT
<213> ORGANISM: Rattus norvegicus

<400> SEQUENCE: 1

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Ala Gln Ser Lys Pro Gln Lys Ala Leu Thr
                 85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Thr Asp Ser Ala
        115                 120                 125

Leu Ser Gln Asn Gly Gln Leu Leu Arg Gln Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
        195                 200                 205

Ser Trp Pro Gly Pro Thr Thr Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Asn Arg Thr Ser Ile Val Gln Ala Ala Gly Gly Gly Thr Gly Gly
            260                 265                 270

Gly Ser Asn Asn Gly Lys Thr Pro Val Cys His Gln Cys His Lys Ile
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Ser Cys Tyr Asp Val Arg
                325                 330                 335

Tyr Ala Pro Ser Cys Ala Lys Cys Lys Lys Lys Ile Thr Gly Glu Ile
            340                 345                 350

Met His Ala Leu Lys Met Thr Trp His Val Pro Cys Phe Thr Cys Ala
```

```
                355                 360                 365
Ala Cys Lys Thr Pro Ile Arg Asn Arg Ala Phe Tyr Met Glu Glu Gly
    370                 375                 380

Ala Pro Tyr Cys Glu Arg Asp Tyr Glu Lys Met Phe Gly Thr Lys Cys
385                 390                 395                 400

Arg Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Asp Lys Pro Leu
        435                 440                 445

Cys Lys Ser His Ala Phe Ser His Val
    450                 455

<210> SEQ ID NO 2
<211> LENGTH: 1696
<212> TYPE: DNA
<213> ORGANISM: Rattus norvegicus

<400> SEQUENCE: 2
gcacgaggat cccagcgcgg ctcctggagg ccgccaggca gccgcccagc cgggcattca      60
ggagcaggta ccatggattc cttcaaggta gtgctggagg acctgccccc ttggggcttc     120
cgtctgcaag ggggcaagga cttcaacgtg cccctctcca tctctcggct cactcctgga     180
ggcaaggccg cacaggccgg tgtggccgtg ggagactggg tactgagtat cgacggtgag     240
aacgccggaa gcctcacaca cattgaagcc cagaacaaga tccgtgcctg tggggagcgc     300
ctcagcctgg tcttagcag agcccagcct gctcagagca accacagaa ggccctgacc      360
cctcccgccg accccccgag gtacactttt gcaccaagcg cctccctcaa caagacggcc     420
cggcccttcg gggcaccccc acctactgac agcgccctgt cgcagaatgg acagctgctc     480
agacagctgg tccctgatgc cagcaagcag cggctgatga gaatactga agactggcgc     540
ccgcggccag ggacaggcca gtcccgttcc ttccgcatcc ttgctcacct cacgggcaca     600
gagttcatgc aagacccgga tgaggaattc atgaagaagt caagccaggt gcccaggaca     660
gaagccccag cccagcctc aaccataccc aggaatcct ggcctggccc caccaccccc       720
agccccacca gccgcccacc ctgggccgta gatcctgcat tgctgagcg ctatgcccca      780
gacaaaacca gcacagtgct gacccgacac agccagccag ccacacctac gcctctgcag     840
aaccgcacct ccatagttca ggctgcagct ggaggggca caggaggagg cagcaacaat      900
ggcaagacgc ctgtatgcca ccagtgccac aagatcatcc gcggccgata cctggtagca     960
ctgggccacg cgtaccatcc tgaggaattt gtgtgcagcc agtgtgggaa ggtcctggaa    1020
gagggtggct tcttcgagga aagggagct atcttttgcc cctcctgcta tgatgtgcgc     1080
tatgcaccca gctgtgccaa atgcaagaag aagatcactg agagatcat gcatcgcctg     1140
aagatgacct ggcatgttcc ctgcttcacc tgtgcagcct gcaaaacccc tatccgcaac    1200
agggctttct acatggagga gggggctccc tactgcgagc gagattacga aaagatgttt    1260
ggcacaaagt gtcgcggctg tgacttcaag atcgatgccg ggaccgtttt cctggaagcc    1320
ctgggtttca gctggcatga acgtgttttt gtttgcgcaa tatgtcaaat caacttggaa    1380
ggaaagacct tctactccaa gaaggacaag cccctgtgca agagccatgc cttttcccac    1440
gtatgagcac ctcctcacac tactgccacc ctactctgcc agaagggtga taaaatgaga    1500
gagctctctc tccctcgacc tttctgggtg gggctggcag ccattgtcct agccttggct    1560
```

```
cctggccaga tcctggggct ccctcctcac agtccccttt cccacacttc ctccaccacc      1620
accaccgtca ctcacaggtg ctagcctcct agccccagtt cactctggtg tcacaataaa      1680
cctgtatgta gctgtg                                                      1696

<210> SEQ ID NO 3
<211> LENGTH: 260
<212> TYPE: DNA
<213> ORGANISM: Rattus norvegicus

<400> SEQUENCE: 3
ttctacatgg aggaggggc tccctactgc gagcgagatt acgagaagat gtttggcaca        60
aagtgtcgcg gctgtgactt caagatcgat gccggggacc gtttcctgga agccctgggt     120
ttcagctggc atgatacgtg ttttgtttgc gcaatatgtc aaatcaactt ggaaggaaag     180
accttctact ccaagaagga caagcccctg tgcaagagcc atgccttttc ccacgtatga     240
gcacctcctc acactactgc                                                 260

<210> SEQ ID NO 4
<211> LENGTH: 16
<212> TYPE: DNA
<213> ORGANISM: Artificial Sequence
<220> FEATURE:
<223> OTHER INFORMATION: Differential Display PCR Primer

<400> SEQUENCE: 4
aagctttttt tttttg                                                      16

<210> SEQ ID NO 5
<211> LENGTH: 13
<212> TYPE: DNA
<213> ORGANISM: Artificial Sequence
<220> FEATURE:
<223> OTHER INFORMATION: Differential Display PCR Primer

<400> SEQUENCE: 5
aagcttggct atg                                                         13

<210> SEQ ID NO 6
<211> LENGTH: 223
<212> TYPE: DNA
<213> ORGANISM: Rattus norvegicus

<400> SEQUENCE: 6
atccttgctc acctcacggg caccgagttc atgcaagacc cggatgagga gcacctgaag        60
aaatcaagcc aggtgcccag gacagaagcc ccagccccag cctcatctac acccaggag       120 ccctggcctg gcctaccgc cccagccct accagccgcc cgccctgggc tgtggaccct        180
gcgtttgccg agcgctatgc cccagacaaa accagcacag tgc                       223

<210> SEQ ID NO 7
<211> LENGTH: 717
<212> TYPE: DNA
<213> ORGANISM: Homo sapiens

<400> SEQUENCE: 7
atggattcct tcaaggtagt gctggagggg ccagcacctt ggggcttccg gctgcaaggg       60
ggcaaggact tcaatgtgcc cctctccatt tcccggctca ctcctggggg caaagcggcg     120
caggccggag tggccgtggg tgactgggtg ctgagcatcg atggcgagaa tgcgggtagc     180
```

-continued

| | |
|---|---|
| ctcacacaca tcgaagctca gaacaagatc cgggcctgcg gggagcgcct cagcctgggc | 240 |
| ctcagcaggg cccagccggt tcagagcaaa ccgcagaagg cctccgcccc cgccgcggac | 300 |
| cctccgcggt acacctttgc acccagcgtc tccctcaaca agacggcccg gcccctttggg | 360 |
| gcgcccccgc ccgctgacag cgcccgcaa cagaatggac agccgctccg accgctggtc | 420 |
| ccagatgcca gcaagcagcg gctgatggag aacacagagg actggcggcc gcggccgggg | 480 |
| acaggccagt cgcgttcctt ccgcatcctt gcccacctca caggcaccga gttcatgcaa | 540 |
| gacccggatg aggagcacct gaagaaatca agccaggtgc ccaggacaga agccccagcc | 600 |
| ccagcctcat ctacacccca ggagccctgg cctggcccta ccgcccccag ccctaccagc | 660 |
| cgcccgccct gggctgtgga ccctgcgttt gccgagcgct atgccccgga caaaacg | 717 |

<210> SEQ ID NO 8
<211> LENGTH: 1488
<212> TYPE: DNA
<213> ORGANISM: Homo sapiens

<400> SEQUENCE: 8

| | |
|---|---|
| atcgatggcg agaatgcggg tagcctcaca cacatcgaag ctcagaacaa gatccgggcc | 60 |
| tgcggggagc gcctcagcct gggcctcagc agggcccagc cggttcagag caaaccgcag | 120 |
| aaggcctccg cccccgccgc ggaccctccg cggtacacct ttgcacccag cgtctccctc | 180 |
| aacaagacgg cccggccctt tggggcgccc ccgcccgctg acagcgcccc gcaacagaat | 240 |
| ggacagccgc tccgaccgct ggtcccagat gccagcaagc agcggctgat ggagaacaca | 300 |
| gaggactggc ggccgcggcc ggggacaggc cagtcgcgtt ccttccgcat ccttgcccac | 360 |
| ctcacaggca ccgagttcat gcaagacccg gatgaggagc acctgaagaa atcaagccag | 420 |
| gtgcccagga cagaagcccc agccccagcc tcatctacac cccaggagcc ctggcctggc | 480 |
| cctaccgccc ccagccctac cagccgcccg ccctgagctg tggaccctgc gtttgccgag | 540 |
| cgctatgccc cggacaaaac gagcacagtg ctgacccggc acagccagcc ggccacgccc | 600 |
| acgccgctgc agagccgcac ctccattgtg caggcagctg ccggaggggt gccaggaggg | 660 |
| ggcagcaaca acggcaagac tcccgtgtgt caccagtgcc acaaggtcat ccggggccgc | 720 |
| tacctggtgg cgttgggcca cgcgtaccac ccggaggagt ttgtgtgtag ccagtgtggg | 780 |
| aaggtcctgg aagagggtgg cttctttgag gagaagggcg ccatcttctg cccaccatgc | 840 |
| tatgacgtgc gctatgcacc cagctgtgcc aagtgcaaga agaagattac aggcgagatc | 900 |
| atgcacgccc tgaagatgac ctggcacgtg cactgcttta cctgtgctgc ctgcaagacg | 960 |
| cccatccgga cagggccttc tacatggag gagggcgtgc cctattgcga gcgagactat | 1020 |
| gagaagatgt ttggcacgaa atgccatggc tgtgacttca gatcgacgc tggggaccgc | 1080 |
| ttcctggagg ccctgggctt cagctggcat gacacctgct tcgtctgtgc gatatgtcag | 1140 |
| atcaacctgg aaggaaagac cttctactcc aagaaggaca ggcctctctg caagagccat | 1200 |
| gccttctctc atgtgtgagc cccttctgcc cacagctgcc gcggtggccc ctagcctgag | 1260 |
| gggcctggag tcgtggccct gcatttctgg gtagggctgg caatggttgc cttaaccctg | 1320 |
| gctcctggcc cgagcctggg ctccggggcc cctgcccacc caccttatcc tcccaccccca | 1380 |
| ctccctccac caccacagca caccggtgct ggccacacca gcccccttc acctccagtg | 1440 |
| ccacaataaa cctgtaccca gctgaattcc aaaaaatcca aaaaaaaa | 1488 |

<210> SEQ ID NO 9
<211> LENGTH: 1644

<212> TYPE: DNA
<213> ORGANISM: Homo sapiens

<400> SEQUENCE: 9

```
atggattcct tcaaggtagt gctggagggg ccagcacctt ggggcttccg gctgcaaggg      60
ggcaaggact tcaatgtgcc cctctccatt tcccggctca ctcctggggg caaagcggcg     120
caggccggag tggccgtggg tgactgggtg ctgagcatcg atggcgagaa tgcgggtagc     180
ctcacacaca tcgaagctca aacaagatc cgggcctgcg gggagcgcct cagcctgggc     240
ctcagcaggg cccagccggt tcagagcaaa ccgcagaagg cctccgcccc cgccgcggac     300
cctccgcggt acacctttgc acccagcgtc tccctcaaca agacggcccg gccctttggg     360
gcgcccccgc ccgctgacag cgccccgcaa cagaatggac agccgctccg accgctggtc     420
ccagatgcca gcaagcagcg gctgatggag aacacagagg actggcggcc gcggccgggg     480
acaggccagt cgccgttcct tccgcatcct tgcccacctc aggcaccga gttcatgcaa     540
gacccggatg aggagcacct gaagaaatca agccaggtgc caggacaga gccccagcc     600
ccagcctcat ctacaccca ggagccctgg cctggcccta ccgccccag ccctaccagc     660
cgcccgccct gggctgtgga ccctgcgttt gccgagcgct atgccccgga caaaacgagc     720
acagtgctga cccggcacag ccagccggcc acgcccacgc cgctgcagag ccgcacctcc     780
attgtgcagg cagctgccgg aggggtgcca ggaggggca gcaacaacgg caagactccc     840
gtgtgtcacc agtgccacaa ggtcatccgg ggccgctacc tggtggcgtt gggccacgcg     900
taccacccgg aggagtttgt gtgtagccag tgtgggaagg tcctggaaga gggtggcttc     960
tttgaggaga agggcgccat cttctgccca ccatgctatg acgtgcgcta tgcacccagc    1020
tgtgccaagt gcaagaagaa gattacaggc gagatcatgc acgccctgaa gatgacctgg    1080
cacgtgcact gctttacctg tgctgcctgc aagacgccca tccggaacag gccttctac    1140
atggaggagg gcgtgcccta ttgcgagcga gactatgaga gatgtttgg cacgaaatgc    1200
catggctgtg acttcaagat cgacgctggg gaccgcttcc tggaggccct gggcttcagc    1260
tggcatgaca cctgcttcgt ctgtgcgata tgtcagatca acctggaagg aaagaccttc    1320
tactccaaga aggacaggcc tctctgcaag agccatgcct tctctcatgt gtgagcccct    1380
tctgcccaca gctgccgcgg tggccccag cctgagggc ctggagtcgt ggccctgcat    1440
ttctgggtag ggctggcaat ggttgcctta accctggctc ctggcccgag cctgggctcc    1500
cggggccctg cccacccacc ttatcctccc accccactcc ctccaccacc acagcacacc    1560
ggtgctggcc acaccagccc cctttcacct ccagtgccac aataaacctg tacccagctg    1620
aattccaaaa aatccaaaaa aaaa                                         1644
```

<210> SEQ ID NO 10
<211> LENGTH: 457
<212> TYPE: PRT
<213> ORGANISM: Homo sapiens

<400> SEQUENCE: 10

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
```

-continued

```
            50                  55                  60
Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
            115                 120                 125

Pro Gln Gln Asn Gly Gln Pro Leu Arg Pro Leu Val Pro Asp Ala Ser
130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
                180                 185                 190

Val Pro Arg Thr Glu Ala Pro Ala Pro Ala Ser Ser Thr Pro Gln Glu
                195                 200                 205

Pro Trp Pro Gly Pro Thr Ala Pro Ser Pro Thr Ser Arg Pro Pro Trp
210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
                260                 265                 270

Gly Ser Asn Asn Gly Lys Thr Pro Val Cys His Gln Cys His Lys Val
                275                 280                 285

Ile Arg Gly Arg Tyr Leu Val Ala Leu Gly His Ala Tyr His Pro Glu
290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
                340                 345                 350

Met His Ala Leu Lys Met Thr Trp His Val His Cys Phe Thr Cys Ala
                355                 360                 365

Ala Cys Lys Thr Pro Ile Arg Asn Arg Ala Phe Tyr Met Glu Glu Gly
370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
                420                 425                 430

Ile Asn Leu Glu Gly Lys Thr Phe Tyr Ser Lys Lys Asp Arg Pro Leu
                435                 440                 445

Cys Lys Ser His Ala Phe Ser His Val
450                 455

<210> SEQ ID NO 11
```

<211> LENGTH: 22
<212> TYPE: DNA
<213> ORGANISM: Artificial Sequence
<220> FEATURE:
<223> OTHER INFORMATION: Sequencing Primer

<400> SEQUENCE: 11
gccagggttt tcccagtcac ga                                           22

<210> SEQ ID NO 12
<211> LENGTH: 22
<212> TYPE: DNA
<213> ORGANISM: Artificial Sequence
<220> FEATURE:
<223> OTHER INFORMATION: Sequencing Primer

<400> SEQUENCE: 12
gccagggttt tcccagtcac ga                                           22

<210> SEQ ID NO 13
<211> LENGTH: 22
<212> TYPE: DNA
<213> ORGANISM: Homo sapiens

<400> SEQUENCE: 13
tcttagcaga gcccagcctg ct                                           22

<210> SEQ ID NO 14
<211> LENGTH: 22
<212> TYPE: DNA
<213> ORGANISM: Homo sapiens

<400> SEQUENCE: 14
gcatgaactc tgtgcccgtg ag                                           22

<210> SEQ ID NO 15
<211> LENGTH: 20
<212> TYPE: DNA
<213> ORGANISM: Rattus norvegicus

<400> SEQUENCE: 15
atccttgctc acctcacggg                                              20

<210> SEQ ID NO 16
<211> LENGTH: 22
<212> TYPE: DNA
<213> ORGANISM: Rattus norvegicus

<400> SEQUENCE: 16
gcactgtgct ggttttgtct gg                                           22

<210> SEQ ID NO 17
<211> LENGTH: 23
<212> TYPE: DNA
<213> ORGANISM: Homo sapiens

<400> SEQUENCE: 17
catggattcc ttcaaggtag tgc                                          23

<210> SEQ ID NO 18
<211> LENGTH: 20
<212> TYPE: DNA
<213> ORGANISM: Homo sapiens

<400> SEQUENCE: 18

```
gttttgtctg gggcagagcg                                                  20

<210> SEQ ID NO 19
<211> LENGTH: 44
<212> TYPE: DNA
<213> ORGANISM: Artificial Sequence
<220> FEATURE:
<223> OTHER INFORMATION: Sequencing Primer

<400> SEQUENCE: 19
ctaatacgac tcactatagg gctcgagcgg ccgcccgggc aggt                       44

<210> SEQ ID NO 20
<211> LENGTH: 27
<212> TYPE: DNA
<213> ORGANISM: Artificial Sequence
<220> FEATURE:
<223> OTHER INFORMATION: Sequencing Primer

<400> SEQUENCE: 20
ccatcctaat acgactcact atagggc                                          27

<210> SEQ ID NO 21
<211> LENGTH: 765
<212> TYPE: DNA
<213> ORGANISM: Homo sapiens

<400> SEQUENCE: 21
ccgttgtttg taaaacgacg cagagcagcg ccctggccgg gccaagcagg agccggcatc      60
atggattcct tcaaggtagt gctggagggg ccagcaccct ggggcttccg gctgcaaggg     120
ggcaaggact tcaatgtgcc ctcctccatt tcccggctca cctctggggg caaggccgtg     180
caggccggag tggccgtaag tgactgggtg ctgagcatcg atggcgagaa tgcgggtagc     240
ctcacacaca tcgaagctca gaacaagatc cgggcctgcg gggagcgcct cagcctgggc     300
ctcaacaggg cccagccggt tcagaacaaa ccgcaaaagg cctccgcccc gccgcggac      360 cctccgcggt acacctttgc accaagcgtc tccctcaaca agacgcccg gcccttgggg     420 gcgcccccgc ccgctgacag cgccccgcag cagaatggac agccgctccg accgctggtc     480
ccagatgcca gcaagcagcg gctgatggag aacacagagg actggcggcc gcggccgggg     540
acaggccagt gccgttcctt tcgcatcctt gctcacctta caggcaccga gttcatgcaa     600
gacccggatg aggagcacct gaagaaatca agccaggtgc caggacaga agccccagcc     660 ccagcctcat ctacacccca ggagccctgg cctggcccta ccgcccccag ccctaccagc     720
cgcccgccct gggctgtgga ccctgcgttt gccgagcgct atgcc                     765

<210> SEQ ID NO 22
<211> LENGTH: 1689
<212> TYPE: DNA
<213> ORGANISM: Homo sapiens

<400> SEQUENCE: 22
cgacgcagag cagcgccctg gccgggccaa gcaggagccg gcatcatgga ttccttcaag      60
gtagtgctgg aggggccagc acctggggc ttccggctgc aaggggcaa ggacttcaat     120 gtgcccctct ccatttcccg gctcactcct ggggcaaag cggcgcaggc cggagtggcc     180
gtgggtgact gggtgctgag catcgatggc gagaatgcgg gtagcctcac acacatcgaa     240
gctcagaaca gatccgggc ctgcggggag cgcctcagcc tgggcctcag cagggcccag     300
```

-continued

```
ccggttcaga gcaaaccgca gaaggcctcc gccccgccg cggaccctcc gcggtacacc      360
tttgcaccca gcgtctccct caacaagacg gcccggccct tggggcgcc cccgcccgct      420 gacagcgccc cgcaacagaa tggacagccg ctccgaccgc tggtcccaga tgccagcaag     480
cagcggctga tggagaacac agaggactgg cggccgcggc cggggacagg ccagtcgcgt     540
tccttccgca tccttgccca cctcacaggc accgagttca tgcaagaccc ggatgaggag     600
cacctgaaga aatcaagcca ggtgcccagg acagaagccc cagccccagc ctcatctaca     660
ccccaggagc cctggcctgg ccctaccgcc ccagccccta ccagccgccc gccctgggct     720
gtggaccctg cgtttgccga gcgctatgcc ccggacaaaa cgagcacagt gctgacccgg     780
cacagccagc cggccacgcc cacgccgctg cagagccgca cctccattgt gcaggcagct     840 gccgagggg tgccaggagg gggcagcaac aacggcaaga ctcccgtgtg tcaccagtgc      900
cacaaggtca tccggggccg ctacctggtg gcgttgggcc acgcgtacca cccggaggag     960
tttgtgtgta gccagtgtgg gaaggtcctg aagaggggtg gcttctttga ggagaagggc    1020
gccatcttct gcccaccatg ctatgacgtg cgctatgcac ccagctgtgc caagtgcaag    1080
aagaagatta caggcgagat catgcacgcc ctgaagatga cctggcacgt gcactgcttt    1140
acctgtgctg cctgcaagac gcccatccgg aacagggcct tctacatgga ggagggcgtg    1200
ccctattgcg agcgagacta tgagaagatg tttggcacga aatgccatgg ctgtgacttc    1260
aagatcgacg ctggggaccg cttcctggag gccctgggct tcagctggca tgacacctgc    1320
ttcgtctgtg cgatatgtca gatcaacctg gaaggaaaga ccttctactc caagaaggac    1380
aggcctctct gcaagagcca tgccttctct catgtgtgag ccccttctgc ccacagctgc    1440
cgcggtggcc cctagcctga ggggcctgga gtcgtggccc tgcatttctg ggtagggctg    1500
gcaatggttg ccttaaccct ggctcctggc ccgagcctgg gctcccgggc cctgcccac    1560 ccaccttatc ctcccacccc actccctcca ccaccacagc acaccggtgc tggccacacc    1620 agccccttt cacctccagt gccacaataa acctgtaccc agctgaattc caaaaaatcc     1680
aaaaaaaaa                                                            1689
```

<210> SEQ ID NO 23
<211> LENGTH: 22
<212> TYPE: DNA
<213> ORGANISM: Homo sapiens

<400> SEQUENCE: 23
gcactgtgct cgttttgtcc gg     22

<210> SEQ ID NO 24
<211> LENGTH: 21
<212> TYPE: DNA
<213> ORGANISM: Homo sapiens

<400> SEQUENCE: 24
tccttgctca cctcacgggc a     21

<210> SEQ ID NO 25
<211> LENGTH: 30
<212> TYPE: DNA
<213> ORGANISM: Homo sapiens

<400> SEQUENCE: 25
tcctcatccg ggtcttgcat gaactcggtg     30

```
<210> SEQ ID NO 26
<211> LENGTH: 28
<212> TYPE: DNA
<213> ORGANISM: Homo sapiens
<220> FEATURE:
<223> OTHER INFORMATION: Sequencing primer

<400> SEQUENCE: 26
gcccccgccc gctgacagcg ccccgcaa                                      28

<210> SEQ ID NO 27
<211> LENGTH: 24
<212> TYPE: DNA
<213> ORGANISM: Homo sapiens

<400> SEQUENCE: 27
tccttgctca cctcacgggc accg                                          24

<210> SEQ ID NO 28
<211> LENGTH: 22
<212> TYPE: DNA
<213> ORGANISM: Artificial Sequence
<220> FEATURE:
<223> OTHER INFORMATION: Sequencing Primer

<400> SEQUENCE: 28
gtaatacgac tcactatagg gc                                            22

<210> SEQ ID NO 29
<211> LENGTH: 23
<212> TYPE: DNA
<213> ORGANISM: Rattus norvegicus

<400> SEQUENCE: 29
gcggctgatg gagaatactg aag                                           23

<210> SEQ ID NO 30
<211> LENGTH: 23
<212> TYPE: DNA
<213> ORGANISM: Rattus norvegicus

<400> SEQUENCE: 30
atcttgtggc actggtggca tac                                           23

<210> SEQ ID NO 31
<211> LENGTH: 22
<212> TYPE: DNA
<213> ORGANISM: Rattus norvegicus

<400> SEQUENCE: 31
tgtgtcgggt cagcactgtg ct                                            22

<210> SEQ ID NO 32
<211> LENGTH: 1620
<212> TYPE: DNA
<213> ORGANISM: Homo sapiens

<400> SEQUENCE: 32
atggattcct tcaaggtagt gctggagggg ccagcaccct tggggcttcc gctgcaaggg     60
ggcaaggact tcaatgtgcc cctctccatt tcccggctca ctcctggggg caaagcggcg    120
caggccggag tggccgtggg tgactgggtg ctgagcatcg atggcgagaa tgcgggtagc    180
ctcacacaca tcgaagctca gaacaagatc cgggcctgcg gggagcgcct cagcctgggc    240
```

```
ctcagcaggg cccagccggt tcagagcaaa ccgcagaagg cctccgcccc cgccgcggac      300
cctccgcggt acacctttgc acccagcgtc tccctcaaca agacgcccg gccctttggg       360 gcgcccccgc ccgctgacag cgccccgcaa cagaatggac agccgctccg accgctggtc     420
ccagatgcca gcaagcagcg gctgatggag aacacagagg actggcggcc gcggccgggg    480
acaggccagt cgcgttcctt ccgcatcctt gcccacctca caggcaccga gttcatgcaa    540
gacccggatg aggagcacct gaagaaatca agccaggtgc ccaggacaga agccccagcc   600
ccagcctcat ctacaccccca ggagccctgg cctggcccta ccgccccag ccctaccagc    660 cgcccgccct gagctgtgga ccctgcgttt gccgagcgct atgccccgga caaaacgagc    720
acagtgctga cccggcacag ccagccggcc acgcccacgc cgctgcagag ccgcacctcc     780
attgtgcagg cagctgccgg aggggtgcca ggagggggga gcaacaacgg caagactccc    840
gtgtgtcacc agtgccacaa ggtcatccgg ggccgctacc tggtggcgtt gggccacgcg    900
taccacccgg aggagtttgt gtgtagccag tgtgggaagg tcctggaaga gggtggcttc   960
tttgaggaga agggcgccat cttctgccca ccatgctatg acgtgcgcta tgcacccagc   1020
tgtgccaagt gcaagaagaa gattacaggc gagatcatgc acgccctgaa gatgacctgg   1080
cacgtgcact gctttacctg tgctgcctgc aagacgccca tccggaacag ggccttctac   1140
atggaggagg cgtgcccta ttgcgagcga gactatgaga gatgtttgg cacgaaatgc     1200 catggctgtg acttcaagat cgacgctggg gaccgcttcc tggaggccct gggcttcagc    1260
tggcatgaca cctgcttcgt ctgtgcgata tgtcagatca acctggaagg aaagaccttc    1320
tactccaaga aggacaggcc tctctgcaag agccatgcct tctctcatgt gtgagcccct     1380
tctgcccaca gctgccgcgg tggccccctag cctgaggggc ctggagtcgt ggccctgcat     1440
ttctgggtag ggctggcaat ggttgcctta accctggctc ctggcccgag cctgggctcc   1500
cggggccctg cccaccccacc ttatcctccc accccactcc ctccaccacc acagcacacc    1560
ggtgctggcc acaccagccc cctttcacct ccagtgccac aataaacctg tacccagctg    1620
```

<210> SEQ ID NO 33
<211> LENGTH: 1665
<212> TYPE: DNA
<213> ORGANISM: Homo sapiens

<400> SEQUENCE: 33

```
cgacgcagag cagcgccctg gccgggccaa gcaggagccg gcatcatgga ttccttcaag      60
gtagtgctgg aggggccagc accttggggc ttccggctgc aagggggcaa ggacttcaat     120
gtgcccctct ccatttcccg gctcactcct gggggcaaag cggcgcaggc cggagtggcc    180
gtgggtgact gggtgctgag catcgatggc gagaatgcgc gtagcctcac acacatcgaa    240
gctcagaaca agatccgggc ctgcggggag cgcctcagcc tgggcctcag cagggcccag    300
ccggttcaga gcaaaccgca gaaggcctcc gcccccgccg cggaccctcc gcggtacacc     360
tttgcaccca gcgtctccct caacaagacg gcccggccct ttggggcgcc ccgcccgct    420 gacagcgccc cgcaacagaa tggacagccg ctccgaccgc tggtcccaga tgccagcaag    480
cagcggctga tggagaacac agaggactgg cggccgcggc cggggacagg ccagtcgcgt    540
tccttccgca tccttgccca cctcacaggc accgagttca tgcaagaccc ggatgaggag    600
cacctgaaga aatcaagcca ggtgcccagg acagaagccc cagccccagc ctcatctaca    660
ccccaggagc cctggcctgg ccctaccgcc ccagccctac cagccgcccg ccctgagct     720 gtggaccctg cgtttgccga gcgctatgcc ccggacaaaa cgagcacagt gctgacccgg    780
```

```
cacagccagc cggccacgcc cacgccgctg cagagccgca cctccattgt gcaggcagct    840
gccggagggg tgccaggagg gggcagcaac aacggcaaga ctcccgtgtg tcaccagtgc    900
cacaaggtca tccggggccg ctacctggtg gcgttgggcc acgcgtacca cccggaggag    960
tttgtgtgta gccagtgtgg aaggtcctg gaagagggtg gcttctttga ggagaagggc   1020
gccatcttct gccaccatg ctatgacgtg cgctatgcac ccagctgtgc caagtgcaag   1080
aagaagatta caggcgagat catgcacgcc ctgaagatga cctggcacgt gcactgcttt   1140
acctgtgctg cctgcaagac gcccatccgg aacagggcct tctacatgga ggagggcgtg   1200
ccctattgcg agcgagacta tgagaagatg tttggcacga aatgccatgg ctgtgacttc   1260
aagatcgacg ctggggaccg cttcctggag ccctgggct tcagctggca tgacacctgc   1320
ttcgtctgtg cgatatgtca gatcaacctg gaaggaaaga ccttctactc caagaaggac   1380
aggcctctct gcaagagcca tgccttctct catgtgtgag ccccttctgc ccacagctgc   1440
cgcggtggcc cctagcctga ggggcctgga gtcgtggccc tgcatttctg ggtagggctg   1500
gcaatggttg ccttaaccct ggctcctggc ccgagcctgg gctcccgggc ccctgcccac   1560
ccaccttatc ctcccacccc actccctcca ccaccacagc acaccggtgc tggccacacc   1620
agcccccttt cacctccagt gccacaataa acctgtaccc agctg              1665
```

```
<210> SEQ ID NO 34
<211> LENGTH: 223
<212> TYPE: PRT
<213> ORGANISM: Homo sapiens

<400> SEQUENCE: 34
```

Met Asp Ser Phe Lys Val Val Leu Glu Gly Pro Ala Pro Trp Gly Phe
 1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro

```
<210> SEQ ID NO 35
<211> LENGTH: 25
<212> TYPE: DNA
<213> ORGANISM: Rattus norvegicus

<400> SEQUENCE: 35
gcactacctt gaaggaatcc atggt                                    25
```

BONE MINERALIZATION PROTEINS, DNA, VECTORS, EXPRESSION SYSTEMS

CROSS REFERENCE TO RELATED APPLICATIONS

This application is a continuation of application Ser. No. 09/986,625 filed on Nov. 9, 2001, now U.S. Pat. No. 6,858,431, now U.S. Pat. No. 6,858,431 to which priority is claimed under 35 U.S.C. §120 and is also a continuation of U.S. application Ser. No. 10/946,268 filed Sep. 21 2004, now abandoned which is a continuation of U.S. application Ser. No. 09/986,625, filed Nov. 9. 2001, now U.S. Pat. No. 6,858,431, which is a divisional application of Ser. No. 09/721,975, filed Nov. 27, 2000, now U.S. Pat. No. 6,444,803, which is a continuation of Ser. No. 09/124,238, filed Jul. 29 1998, now U.S. Pat. No. 6,300,127, which claims the benefit of U.S. provisional application No. 60/054,219, filed Jul. 30, 1997, and U.S. provisional application No. 60/080,407, filed Apr. 2, 1998. The entire teachings of the above applications are incorporated herein by reference.

BACKGROUND OF THE INVENTION

1. Field of the Invention

The field of the invention relates generally to osteogenic cells and the formation of bone and boney tissue in mammalian species. Specifically, the invention concerns a novel family of proteins, and nucleic acids encoding those proteins, that enhances the efficacy of bone mineralization in vitro and in vivo. The invention provides methods for treating a variety of pathological conditions associated bone and boney tissue, such as, for example, spine fusion, fracture repair and osteoporosis.

2. Description of the Related Art

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, *Genes & Develop.*, 10:1580 (1996). This group of transforming growth factor-beta superfamily secreted proteins has a spectrum of activities in a variety of cell types at different stages of differentiation; differences in physiological activity between these closely related molecules have not been clarified. D. M. Kingsley, *Trends Genet.*, 10:16 (1994).

To better discern the unique physiological role of different BMP signaling proteins, we recently compared the potency of BMP-6 with that of BMP-2 and BMP4, for inducing rat calvarial osteoblast differentiation. Boden et al., *Endocrinology*, 137:3401 (1996). We studied this process in first passage (secondary) cultures of fetal rat calvaria that require BMP or glucocorticoid for initiation of differentiation. In this model of membranous bone formation, glucocorticoid (GC) or a BMP will initiate differentiation to mineralized bone nodules capable of secreting osteocalcin, the osteoblast-specific protein. This secondary culture system is distinct from primary rat osteoblast cultures which undergo spontaneous differentiation. In this secondary system, glucocorticoid resulted in a ten-fold induction of BMP-6 mRNA and protein expression which was responsible for the enhancement of osteoblast differentiation. Boden et a., *Endocrinology*, 138:2920 (1997).

In addition to extracellular signals, such as the BMPs, intracellular signals or regulatory molecules may also play a role in the cascade of events leading to formation of new bone. One broad class of intracellular regulatory molecules are the LIM proteins, which are so named because they possess a characteristic structural motif known as the LIM domain. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein-protein interactions, through the formation of dimers with identical or different LIM domains, or by binding distinct proteins.

In LIM homeodomain proteins, that is, proteins having both LIM domains and a homeodomain sequence, the LIM domains function as negative regulatory elements. LIM homeodomain proteins are involved in the control of cell lineage determination and the regulation of differentiation, although LIM-only proteins may have similar roles. LIM-only proteins are also implicated in the control of cell proliferation since several genes encoding such proteins are associated with oncogenic chromosome translocations.

Humans and other mammalian species are prone to diseases or injuries that require the processes of bone repair and/or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would results in systemic formation of new bone. Such treatment regimens would reduce the incidence of fractures arising from the loss of bone mass that is a characteristic of this disease.

For at least these reasons, extracellular factors, such as the BMPs, have been investigated for the purpose of using them to stimulate formation of new bone in vivo. Despite the early successes achieved with BMPs and other extracellular signalling molecules, their use entails a number of disadvantages. For example, relatively large doses of purified BMPs are required to enhance the production of new bone, thereby increasing the expense of such treatment methods. Furthermore, extracellular proteins are susceptible to degradation following their introduction into a host animal. In addition, because they are typically immunogenic, the possibility of stimulating an immune response to the administered proteins is ever present.

Due to such concerns, it would be desirable to have available treatment regimens that use an intracellular signalling molecule to induce new bone formation. Advances in the field of gene therapy now make it possible to introduce into osteogenic precursor cells, that is, cells involved in bone formation, nucleotide fragments encoding intracellular signals that form part of the bone formation process. Gene therapy for bone formation offers a number of potential advantages: (1) lower production costs; (2) greater efficacy, compared to extracellular treatment regiments, due to the ability to achieve prolonged expression of the intracellular signal; (3) it would by-pass the possibility that treatment with extracellular signals might be hampered due to the presence of limiting numbers of receptors for those signals; (4) it permits the delivery of transfected potential osteoprogenitor cells directly to the site where localized bone formation is required; and (5) it would permit systemic bone formation, thereby providing a treatment regimen for osteoporosis and other metabolic bone diseases.

SUMMARY OF THE INVENTION

The present invention seeks to overcome the drawbacks in the prior art by providing novels compositions and methods for inducing bone formation using an intracellular signalling molecule that participates early in the cascade of events that leads to bone formation. Applicants have discovered 10-4/RLMP (SEQ ID NO: 1, SEQ ID NO: 2), a novel LIM gene with a sequence originally isolated from stimulated rat calvarial osteoblast cultures. The gene has been cloned, sequenced and assayed for its ability to enhance the efficacy of bone mineralization in vitro. The protein RLMP affects mineralization of bone matrix as well as differentiation of cells into the osteoblast lineage. Unlike other known cytokines, for example, BMPs, RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

Applicants have also cloned, sequenced and deduced the amino acid sequence of a corresponding human protein, named human LMP-1. The human protein demonstrates enhanced efficacy of bone mineralization in vitro and in vivo.

In addition, the applicants have characterized a truncated (short) version of LMP-1, termed HLMP-1s. This short version resulted from a point mutation in one source of a cDNA clone, providing a stop codon which truncated the protein. The short version (LMP-1s) is fully functional when expressed in cell culture and in vivo.

Additional features and advantages of the invention will be set forth in the description which follows, and in part will be apparent from the description, or may be learned by practice of the invention. The objectives and other advantages of the invention will be realized and attained by the methods and compositions of matter particularly pointed out in the written description and claims hereof.

In one broad aspect, the invention relates to an isolated nucleic acid molecule comprising a nucleic acid sequence encoding any LIM mineralization protein, wherein the nucleic acid molecule hybridizes under standard conditions to a nucleic acid molecule complementary to the full length of SEQ. ID NO: 25, and wherein the molecule hybridizes under highly stringent conditions to a nucleic acid molecule complementary to the full length of SEQ. ID NO: 26. In a specific aspect, the isolated nucleic acid molecule encodes HLMP-1, HLMP-1s or RLMP. In addition, the invention is directed to vectors comprising these nucleic acid molecules, as well as host cells comprising the vectors. In another specific aspect, the invention relates to the proteins themselves.

In a second broad aspect, the invention relates to antibody that is specific for LIM mineralization protein, including HLMP-1, HLMP-1s and RLMP. In one specific ascpect, the antibody is a polyclonal antibody. In another specific aspect, the antibody is a monoclonal antibody.

In a third broad aspect, the invention relates to method of inducing bone formation wherein osteogenic precursor cells are transfected with an isolated nucleic acid molecule comprising a nucleotide sequence encoding LIM mineralization protein. In one specific aspect, the isolated nucleic acid molecule is in a vector, which may be a plasmid or a virus, such as adenovirus or retrovirus. The transfection may occur ex vivo or in vivo by direct injection of the isolated nucleic acid molecule. The transfected isolated nucleic acid molecule may encode HLMP-1, HLMP-1s or RLMP.

In a further aspect, the invention relates to methods of fusing a spine by transfecting osteogenic precursor cells with an isolated nucleic acid molecule having a nucleotide sequence encoding LIM mineralization protein, admixing the transfected osteogenic precursor cells with a matrix and contacting the matrix with the spine.

In yet another aspect, the invention relates to methods for inducing systemic bone formation by stable transfection of host cells with the vectors of the invention.

It is to be understood that both the foregoing general description and the following detailed description are exemplary and explanatory and are intended to provide further explanation of the invention as claimed.

ABBREVIATIONS AND DEFINITIONS

| | |
|---|---|
| BMP | Bone Morphogenetic Protein |
| HLMP-1 | Human LMP-1, also designated as Human LIM Protein or HLMP |
| HLMP-1s | Human LMP-1 Short (truncated) protein |
| HLMPU | Human LIM Protein Unique Region |
| LMP | LIM mineralization protein |
| MEM | Minimal essential medium |
| Trm | Triamcinolone |
| β-GlyP | Beta-glycerolphosphate |
| RACE | Rapid Amplification of cDNA Ends |
| RLMP | Rat LIM mineralization protein, also designated as RLMP-1 |
| RLMPU | Rat LIM Protein Unique Region |
| RNAsin | RNase inhibitor |
| ROB | Rat Osteoblast |
| 10-4 | Clone containing cDNA sequence for RLMP (SEQ ID NO: 2) |
| UTR | Untranslated Region |

DETAILED DESCRIPTION OF THE INVENTION

The present invention relates to novel mammalian LIM proteins, herein designated LIM mineralization proteins, or LMP. The invention relates more particularly to human LMP, known as HLMP or HLMP-1. The applicants have discovered that these proteins enhance bone mineralization in mammalian cells grown in vitro. When produced in mammals, LMP also induces bone formation in, vivo.

Ex vivo transfection of bone marrow cells, osteogenic precursor cells or mesenchymal stem cells with nucleic acid that encodes LMP or HLMP, followed by reimplantation of the transfected cells in the donor, is suitable for treating a variety of bone-related disorders or injuries. For example, one can use this method to: augment long bone fracture repair; generate bone in segmental defects; provide a bone graft substitute for fractures; facilitate tumor reconstruction or spine fusion; and provide a local treatment (by injection) for weak or osteoporotic bone, such as in osteoporosis of the hip, vertebrae, or wrist. Transfection with LMP or HLMP-encoding nucleic acid is also useful in the percutaneous injection of transfected marrow cells to accelerate the repair of fractured long bones; treatment of delayed union or non-unions of long bone fractures or pseudoarthrosis of spine fusions; and for inducing new bone formation in avascular necrosis of the hip or knee.

In addition to ex vivo-based methods of gene therapy, transfection of a recombinant DNA vector comprising a nucleic acid sequence that encodes LMP or HLMP can be accomplished in vivo. When a DNA fragment that encodes LMP or HLMP is inserted into an appropriate viral vector, for example, an adenovirus vector, the viral construct can be injected directly into a body site were endochondral bone formation is desired. By using a direct, percutaneous injection to introduce the LMP or HLMP sequence stimulation of bone formation can be accomplished without the need for surgical intervention either to obtain bone marrow cells (to transfect ex vivo) or to reimplant them into the patient at the site where new bone is required. Alden et al., *Neurosurgical Focus* (1998), have demonstrated the utility of a direct injection method of gene therapy using a cDNA that encodes BMP-2, which was cloned into an adenovirus vector.

It is also possible to carry out in vivo gene therapy by directly injecting into an appropriate body site, a naked, that is, unencapsulated, recombinant plasmid comprising a nucleic acid sequence that encodes HLMP. In this embodiment of the invention, transfection occurs when the naked plasmid DNA is taken up, or internalized, by the appropriate target cells, which have been described. As in the case of in vivo gene therapy using a viral construct, direct injection of naked plasmid DNA offers the advantage that little or no surgical intervention is required. Direct gene therapy, using naked plasmid DNA that encodes the endothelial cell mitogen VEGF (vascular endothelial growth factor), has been successfully demonstrated in human patients. Baumgartner et al., *Circulation,* 97(12):1114-23 (1998).

By using an adenovirus vector to deliver LMP into osteogenic cells, transient expression of LMP is achieved. This occurs because adenovirus does not incorporate into the genome of target cells that are transfected. Transient expression of LMP, that is, expression that occurs during the lifetime of the transfected target cells, is sufficient to achieve the objects of the invention. Stable expression of LMP, however, can occur when a vector that incorporates into the genome of the target cell is used as a delivery vehicle. Retrovirus-based vectors, for example, are suitable for this purpose.

Stable expression of LMP is particularly useful for treating various systemic bone-related disorders, such as osteoporosis and osteogenesis imperfecta. For this embodiment of the invention, in addition to using a vector that integrates into the genome of the target cell to deliver an LMP-encoding nucleotide sequence into target cells, LMP expression is placed under the control of a regulatable promoter. For example, a promoter that is turned on by exposure to an exogenous inducing agent, such as tetracycline, is suitable. Using this approach, one can stimulate formation of new bone on a systemic basis by administering an effective amount of the exogenous inducing agent. Once a sufficient quantity of bone mass is achieved, administration of the exogenous inducing agent is discontinued. This process may be repeated as needed to replace bone mass lost, for example, as a consequence of osteoporosis.

Antibodies specific for HLMP are particularly suitable for use in methods for assaying the osteoinductive, that is, bone-forming, potential of patient cells. In this way one can identify patients at risk for slow or poor healing of bone repair. Also, HLMP-specific antibodies are suitable for use in marker assays to identify risk factors in bone degenerative diseases, such as, for example, osteoporosis.

Following well known and conventional methods, the genes of the present invention are prepared by ligation of nucleic acid segments that encode LMP to other nucleic acid sequences, such as cloning and/or expression vectors. Methods needed to construct and analyze these recombinant vectors, for example, restriction endonuclease digests, cloning protocols, mutagenesis, organic synthesis of oligonucleotides and DNA sequencing, have been described. For DNA sequencing DNA, the dieoxyterminator method is the preferred.

Many treatises on recombinant DNA methods have been published, including Sambrook et al., *Molecular Cloning: A Laboratory Manual*, Cold Spring Harbor Press, 2nd edition (1988), Davis et al., *Basic Methods in Molecular Biology*, Elsevier (1986), and Ausubel et al., *Current Protocols in Molecular Biology*, Wiley Interscience (1988). These reference manuals are specifically incorporated by reference herein.

Primer-directed amplification of DNA or cDNA is a common step in the expression of the genes of this invention. It is typically performed by the polymerase chain reaction (PCR). PCR is described in U.S. Pat. No. 4,800,159 to Mullis et al. and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from *Thermus aquaticus*, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The gene encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrance of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the *E. coli* lac promoter, is also suitable for the expression of the chimeric coding sequences. Other suitable regulatable promoters include trp, tac, recA, T7 and lambda promoters.

DNA encoding LMP is transfected into recipient cells by one of several standard published procedures, for example, calcium phosphate precipitation, DEAE-Dextran, electroporation or protoplast fusion, to form stable transformants. Calcium phosphate precipitation is preferred, particularly when performed as follows.

DNAs are coprecipitated with calcium phosphate according to the method of Graham and Van Der, *Virology,* 52:456 (1973), before transfer into cells. An aliquot of 40-50 μg of DNA, with salmon sperm or calf thymus DNA as a carrier, is used for $0.5 \times 10^6$ cells plated on a 100 mm dish. The DNA is mixed with 0.5 ml of 2× Hepes solution (280 mM NaCl, 50 mM Hepes and 1.5 mM $Na_2HPO_4$, pH 7.0), to which an equal volume of 2× $CaCl_2$ (250 mM $CaCl_2$ and 10 mM Hepes, pH 7.0) is added. A white granular precipitate, appearing after 30-40 minutes, is evenly distributed dropwise on the cells, which are allowed to incubate for 4-16 hours at 37° C. The medium is removed and the cells shocked with 15% glycerol in PBS for 3 minutes. After removing the glycerol, the cells are fed with Dulbecco's Minimal Essential Medium (DMEM) containing 10% fetal bovine serum.

DNA can also be transfected using: the DEAE-Dextran methods of Kimura et al., *Virology*, 49:394 (1972) and Sompayrac et al., *Proc. Natl. Acad. Sci. USA*, 78:7575 (1981); the electroporation method of Potter, *Proc. Natl. Acad. Sci. USA*, 81:7161 (1984); and the protoplast fusion method of Sandri-Goddin et al., *Molec. Cell. Biol.*, 1:743 (1981).

Phosphoramidite chemistry in solid phase is the preferred method for the organic synthesis of oligodeoxynucleotides and polydeoxynucleotides. In addition, many other organic synthesis methods are available. Those methods are readily adapted by those skilled in the art to the particular sequences of the invention.

The present invention also includes nucleic acid molecules that hybridize under standard conditions to any of the nucleic acid sequences encoding the LIM mineralization proteins of the invention. "Standard hybridization conditions" will vary with the size of the probe, the background and the concentration of the nucleic acid reagents, as well as the type of hybridization, for example, in situ, Southern blot, or hybridization of DNA-RNA hybrids (Northern blot). The determination of "standard hybridization conditions" is within the level of skill in the art. For example, see U.S. Pat. No. 5,580,775 to Fremeau et al., herein incorporated by reference for this purpose. See also, Southern, E. M., *J. Mol. Biol.*, 98:503 (1975), Alwine et al., *Meth. Enzymol.*, 68:220 (1979), and Sambrook et al., *Molecular Cloning: A laboratory Manual*, 2nd edition, pp. 7.19-7.50, Cold Spring Harbor Press (1989).

One preferred set of standard hybrization conditions involves a blot that is prehybridized at 42° C. for 2 hours in 50% formamide, 5× SSPE (150 nM NaCl, 10 mM Na $H_2PO_4$ [pH 7.4], 1 mM EDTA [pH 8.0]), 5× Denhardt's solution (20 mg Ficoll, 20 mg polyvinylpyrrolidone and 20 mg BSA per 100 ml water), 10% dextran sulphate, 1% SDS and 100 µg/ml salmon sperm DNA. A $^{32}P$-labelled cDNA probe is added, and hybridization is continued for 14 hours. Afterward, the blot is washed twice with 2× SSPE, 0.1% SDS for 20 minutes at 22° C., followed by a 1 hour wash at 65° C. in 0.1× SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only susbstantially identical sequences will hybridize.

Another aspect of the invention includes the proteins encoded by the nucleic acid sequences. In still another embodiment, the inventon relates to the identification of such proteins based on anti-LMP antibodies. In this embodiment, protein samples are prepared for Western blot analysis by lysing cells and separating the proteins by SDS-PAGE. The proteins are transferred to nitrocellulose by electroblotting as described by Ausubel et al., *Current Protocols in Molecular Biology*, John Wiley and Sons (1987). After blocking the filter with instant nonfat dry milk (1 gm in 100 ml PBS), anti-LMP antibody is added to the filter and incubated for 1 hour at room temperature. The filter is washed thoroughly with phosphate buffered saline (PBS) and incubated with horseradish peroxidase (HRPO)-antibody conjugate for 1 hour at room temperature. The filter is again washed thoroughly-with PBS and the antigen bands are identified by adding diaminobenzidine (DAB).

Monospecific antibodies are the reagent of choice in the present invention, and are specifically used to analyze patient cells for specific characteristics associated with the expression of LMP. "Monospecific antibody" as used herein is defined as a single antibody species or multiple antibody species with homogenous binding characteristics for LMP. "Homogeneous binding" as used herein refers to the ability of the antibody species to bind to a specific antigen or epitope, such as those associated with LMP, as described above. Monospecific antibodies to LMP are purified from mammalian antisera containing antibodies reactive against LMP or are prepared as monoclonal antibodies reactive with LMP using the technique of Kohler and Milstein, *Nature*, 256:495-97 (1975). The LMP specific antibodies are raised by immunizing animals such as, for example, mice, rats, guinea pigs, rabbits, goats or horses, with an appropriate concentration of LMP either with or without an immune adjuvant.

In this process, preimmune serum is collected prior to the first immunization. Each animal receives between about 0.1 mg and about 1000 mg of LMP associated with an acceptable immune adjuvant, if desired. Such acceptable adjuvants include, but are not limited to, Freund's complete, Freund's incomplete, alum-precipitate, water in oil emulsion containing *Corynebacterium parvum* and tRNA adjuvants. The initial immunization consists of LMP in, preferably, Freund's complete adjuvant injected at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with LMP are prepared by immunizing inbred mice, preferably Balb/c mice, with LMP. The mice are immunized by the IP or SC route with about 0.1 mg to about 10 mg, preferably about 1 mg, of LMP in about 0.5 ml buffer or saline incorporated in an equal volume of an acceptable adjuvant, as discussed above. Freund's complete adjuvant is preferred. The mice receive an initial i immunization on day 0 and are rested for about 3-30 weeks. Immunized mice are given one or more booster immunizations of about 0.1 to about 10 mg of LMP in a buffer solution such as phosphate buffered saline by the intravenous (IV) route. Lymphocytes from antibody-positive mice, preferably splenic lymphocytes, are obtained by removing the spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin in supplemented Dulbecco's Modified Eagles Medium (DMEM) by procedures known in the art. Supernatant fluids are collected from growth positive wells on about days 14, 18, and 21, and are screened for antibody production by an immunoassay such as solid phase immunoradioassay (SPIRA) using LMP as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques", in *Tissue Culture Methods and Applications*, Kruse and Paterson (eds.), Academic Press (1973). See, also, Harlow et al., *Antibodies: A Laboratory Manual*, Cold Spring Laboratory (1988).

Monoclonal antibodies may also be produced in vivo by injection of pristane-primed Balb/c mice, approximately 0.5 ml per mouse, with about $2 \times 10^6$ to about $6 \times 10^6$ hybridoma cells about 4 days after priming. Ascites fluid is collected at approximately 8-12 days after cell transfer and the monoclonal antibodies are purified by techniques known in the art.

In vitro production in anti-LMP mAb is carried out by growing the hydridoma cell line in DMEM containing about 2% fetal calf serum to obtain sufficient quantities of the specific mAb. The mAb are purified by techniques known in the art.

Antibody titers of ascites or hybridoma culture fluids are determined by various serological or immunological assays, which include, but are not limited to, precipitation, passive agglutination, enzyme-linked immunosorbent antibody (ELISA) technique and radioimmunoassay (RIA) techniques. Similar assays are used to detect the presence of the LMP in body fluids or tissue and cell extracts.

It is readily apparent to those skilled in the art that the above described methods for producing monospecific antibodies may be utilized to produce antibodies specific for polypeptide fragments of LMP, full-length nascent LMP polypeptide, or variants or alleles thereof.

On Jul. 22, 1997, a sample of 10-4/RLMP in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852. The culture accession number for that deposit is 209153. On Mar. 19, 1998, a sample of the vector pHis-A with insert HLPM-1s was deposited at the American Type Culture Collection. The culture accession number for that deposit is 209698. These deposits, made under the requirements of the Budapest Treaty, will be maintained in the ATCC for at least 30 years and will be made available to the public upon the grant of a patent disclosing them. It should be understood that the availability of a deposit does not constitute a license to practice the-subject invention in derogation of patent rights granted by government action.

In assessing the nucleic acids, proteins, or antibodies of the invention, enzyme assays, protein purification, and other-conventional biochemical methods are employed. DNA and RNA are analyzed by Southern blotting and Northern blotting techniques, respectively. Typically, the samples analyzed are size fractionated by gel electrophoresis. The DNA or RNA in the gels are then transferred to nitrocellulose or nylon membranes. The blots, which are replicas of sample patterns in the gels, were then hybridized with probes. Typically, the probes are radiolabelled, preferably with $^{32}P$, although one could label the probes with other signal-generating molecules known to those in the art. Specific bands of interest can then be visualized by detection systems, such as autoradiography.

For purposes of illustrating preferred embodiments of the present invention, the following, non-limiting examples are included. These results demonstrate the feasibility of inducing or enhancing the formation of bone using the LIM mineralization proteins of the invention, and the isolated nucleic acid molecules encoding those proteins.

EXAMPLE 1

Calvarial Cell Culture

Rat calvarial cells, also known as rat osteoblasts ("ROB"), were obtained from 20-day pre-parturition rats as previously described. Boden et al., *Endocrinology*, 137(8):3401-07 (1996). Primary cultures were grown to confluence (7 days), trypsinized, and passed into 6-well plates ($1 \times 10^5$ cells/35 mm well) as first subculture cells. The subculture cells, which were confluent at day 0, were grown for an additional 7 days. Beginning on day 0, media were changed and treatments (Trm and/or BMPs) were applied, under a laminar flow hood, every 3 or 4 days. The standard culture protocol was as follows: days 1-7, MEM, 10% FBS, 50 µg/ml ascorbic acid, ±stimulus; days 8-14, BGJb medium, 10% FBS, 5 mM β-GlyP (as a source of inorganic phosphate to permit mineralization). Endpoint analysis of bone nodule formation and osteocalcin secretion was performed at day 14. The dose of BMP was chosen as 50 ng/ml based on pilot experiments in this system that demonstrated a mid-range effect on the dose-response curve for all BMPs studied.

EXAMPLE 2

Antisense Treatment and Cell Culture

To explore the potential functional role of LMP-1 during membranous bone formation, we synthesized an antisense oligonucleotide to block LMP-1 mRNA translation and treated secondary osteoblast cultures that were undergoing differentiation initiated by glucocorticoid. Inhibition of RLMP expression was accomplished with a highly specific antisense oligonucleotide (having no significant homologies to known rat sequences) corresponding to a 25 bp sequence spanning the putative translational start site (SEQ ID NO: 35). Control cultures either did not receive oligonucleotide or they received sense oligonucleotide. Experiments were performed in the presence (preincubation) and absence of lipofectamine. Briefly, 22 µg of sense or antisense RLMP oligonucleotide was incubated in MEM for 45 minutes at room temperature. Following that incubation, either more MEM or pre-incubated lipofectamine/MEM (7% v/v; incubated 45 minutes at room temperature) was added to achieve an oligonucleotide concentration of 0.2 µM. The resulting mixture was incubated for 15 minutes at room temperature. Oligonucleotide mixtures were then mixed with the appropriate medium, that is, MEM/Ascorbate/±Trm, to achieve a final oligonucleotide concentration of 0.1 µM.

Cells were incubated with the appropriate medium (±stimulus) in the presence or absence of the appropriate oligonucleotides. Cultures originally incubated with lipofectamine were re-fed after 4 hours of incubation (37° C.; 5% $CO_2$) with media containing neither lipofectamine nor oligonucleotide. All cultures, especially cultures receiving oligonucleotide, were re-fed every 24 hours to maintain oligonucleotide levels.

LMP-1 antisense oligonucleotide inhibited mineralized nodule formation and osteocalcin secretion in a dose-dependent manner, similar to the effect of BMP-6 oligonucleotide. The LMP-1 antisense block in osteoblast differentiation could not be rescued by addition of exogenous BMP-6, while the BMP-6 antisense oligonucleotide inhibition was reversed with addition of BMP-6. This experiment further confirmed the upstream position of LMP-1 relative to BMP-6 in the osteoblast differentiation pathway. LMP-1 antisense oligonucleotide also inhibited spontaneous osteoblast differentiation in primary rat osteoblast cultures.

EXAMPLE 3

Quantitation of Mineralized Bone Nodule Formation

Cultures of ROBs prepared according to Examples 1 and 2 were fixed overnight in 70% ethanol and stained with von Kossa silver stain. A semi-automated computerized video image analysis system was used to quantitate nodule count and nodule area in each well. Boden et al., *Endocrinology*, 137(8):3401-07 (1996). These values were then divided to calculate the area per nodule values. This automated process was validated against a manual counting technique and demonstrated a correlation coefficient of 0.92 ($p<0.000001$). All data are expressed as the mean±standard error of the mean (S.E.M.) calculated from 5 or 6 wells at each condition. Each experiment was confirmed at least twice using cells from different calvarial preparations.

EXAMPLE 4

Quantitation of Osteocalcin Secretion

Osteocalcin levels in the culture media were measured using a competitive radioimmunoassay with a monospecific polyclonal antibody (Pab) raised in our laboratory against the C-terminal nonapeptide of rat osteocalcin as described in Nanes et al., *Endocrinology*, 127:588 (1990). Briefly, 1 µg of nonapeptide was iodinated with 1 mCi $^{125}$I—Na by the lactoperoxidase method. Tubes containing 200 µl of assay buffer (0.02 M sodium phosphate, 1 mM EDTA, 0.001% thimerosal, 0.025% BSA) received media taken from cell cultures or osteocalcin standards (0-12,000 fmole) at 100 µl/tube in assay buffer. The Pab (1:40,000; 100 µl) was then added, followed by the iodinated peptide (12,000 cpm; 100 µl). Samples tested for non-specific binding were prepared similarly but contained no antibody.

Bound and free PAbs were separated by the addition of 700 µl goat anti-rabbit IgG, followed by incubation for 18 hours at 4° C. After samples were centrifuged at 1200 rpm for 45 minutes, the supernatants were decanted and the precipitates counted in a gamma counter. Osteocalcin values were reported in fmole/100 µl, which was then converted to pmole/ml medium (3-day production) by dividing those values by 100. Values were expressed as the mean±S.E.M. of triplicate determinations for 5-6 wells for each condition. Each experiment was confirmed at least two times using cells from different calvarial preparations.

EXAMPLE 5

Effect of Trm and RLMP on Mineralization In Vitro

There was little apparent effect of either the sense or antisense oligonucleotides on the overall production of bone nodules in the non-stimulated cell culture system. When ROBs were stimulated with Trm, however, the antisense oligonucleotide to RLMP inhibited mineralization of nodules by >95%. The addition of exogenous BMP-6 to the oligonucleotide-treated cultures did not rescue the mineralization of RLMP-antisense-treated nodules.

Osteocalcin has long been synonymous with bone mineralization, and osteocalcin levels have been correlated with nodule production and mineralization. The RLMP-antisense oligonucleotide significantly decreases osteocalcin production, but the nodule count in antisense-treated cultures does not change significantly. In this case, Tithe addition of exogenous BMP-6 only rescued the production of osteocalcin in RLMP-antisense-treated cultures by 10-15%. This suggests that the action of RLMP is downstream of, and more specific than, BMP-6.

EXAMPLE 6

Harvest and Purification of RNA

Cellular RNA from duplicate wells of ROBs (prepared according to Examples 1 and 2 in 6-well culture dishes) was harvested using 4M guanidine isothiocyanate (GIT) solution to yield statistical triplicates. Briefly, culture supernatant was aspirated from the wells, which were then overlayed with 0.6 ml of GIT solution per duplicate well harvest. After adding the GIT solution, the plates were swirled for 5-10 seconds (being as consistent as possible). Samples were saved at −70° C. for up to 7 days before further processing.

RNA was purified by a slight modification of standard methods according to Sambrook et al., *Molecular Cloning: a Laboratory Manual*, 2nd Ed., chapter 7.19, Cold Spring Harbor Press (1989). Briefly, thawed samples received 60 µl 2.0 M sodium acetate (pH 4.0), 550 µl phenol (water saturated) and 150 µl chloroform:isoamyl alcohol (49:1). After vortexing, the samples were centrifuged (10000×g; 20 minutes; 4° C.), the aqueous phase transferred to a fresh tube, 600 µl isopropanol was added and the RNA precipitated overnight at −20° C.

Following the overnight incubation, the samples were centrifuged (10000×g; 20 minutes) and the supernatant was aspirated gently. The pellets were resuspended in 400 µl DEPC-treated water, extracted once with phenol:chloroform (1:1), extracted with chloroform:isoamyl alcohol (24:1) and precipitated overnight at −20° C. after addition of 40 µl sodium acetate (3.0 M; pH 5.2) and 1.0 ml absolute ethanol. To recover the cellular RNA, the samples were centrifuged (10000×g; 20 min), washed once with 70% ethanol, air dried for 5-10 minutes and resuspended in 20 µl of DEPC-treated water. RNA concentrations were calculated from optical densities that were determined with a spectrophotometer.

EXAMPLE 7

Reverse Transcription-Polymerase Chain Reaction

Heated total RNA (5 µg in 10.5. µl total volume DEPC-H$_2$O at 65° C. for 5 minutes) was added to tubes containing 4 µl 5× MMLV-RT buffer, 2 µl dNTPs, 2 µl dT17 primer (10 pmol/ml), 0.5 µl RNAsin (40 U/ml) and 1 µl MMLV-RT (200 units/µl). The samples were incubated at 37° C. for 1 hour, then at 95° C. for 5 minutes to inactivate the MMLV-RT. The samples were diluted by addition of 80 µl of water.

Reverse-transcribed samples (5 µl) were subjected to polymerase-chain reaction using standard methodologies (50 µl total volume). Briefly, samples were added to tubes containing water and appropriate amounts of PCR buffer, 25 mM MgCl$_2$, dNTPs, forward and reverse primers for glyceraldehyde 3-phosphate dehydrogenase (GAP, a housekeeping gene) and/or BMP-6), $^{32}$P-dCTP, and Taq polymerase. Unless otherwise noted, primers were standardized to run consistently at 22 cycles (94° C., 30"; 58° C., 30"; 72° C., 20").

EXAMPLE 8

Quantitation of RT-PCR Products by Polyacrylamide Gel Electrophoresis (PAGE) and PhosphorImager Analysis RT-PCR products received 5 µl/tube loading dye, were mixed, heated at 65° C. for 10 min and centrifuged. Ten µl of each reaction was subjected to PAGE (12% polyacrylamide: bis; 15 V/well; constant current) under standard conditions. Gels were then incubated in gel preserving buffer (10% v/v glycerol, 7% v/v acetic acid, 40% v/v methanol, 43% deionized water) for 30 minutes, dried (80° C.) in vacuo for 1-2 hours and developed with an electronically-enhanced phosphoresence imaging system for 6-24 hours. Visualized bands were analyzed. Counts per band were plotted graphically.

EXAMPLE 9

Differential Display PCR

RNA was extracted from cells stimulated with glucocorticoid (Trm, 1 nM). Heated, DNase-treated total RNA (5 µg in 10.5 µl total volume in DEPC-H$_2$O at 65° C. for 5 minutes) was reverse transcribed as described in Example 7, but H-T$_{11}$M (SEQ ID. NO: 4) was used as the MMLV-RT primer. The resulting cDNAs were PCR-amplified as described above, but with various commercial primer sets (for example, H-T$_{11}$G (SEQ ID NO: 4) and H-AP-10 (SEQ ID. NO: 5); GenHunter Corp, Nashville, Tenn.). Radiolabelled PCR products were fractionated by gel electrophoresis on a DNA sequencing gel. After electrophoresis, the resulting gels were dried in vacuo and autoradiographs were exposed overnight. Bands representing differentially-expressed cDNAs were excised from the gel and reamplified by PCR using the method of Conner et al., *Proc. Natl. Acad. Sci. USA*, 88:278 (1983). The products of PCR reamplification were cloned into the vector PCR-II (TA cloning kit; InVitrogen, Carlsbad, Calif.).

EXAMPLE 10

Screening of a UMR 106 Rat Osteosarcoma Cell cDNA Library

A UMR 106 library (2.5×10$^{10}$ pfu/ml) was plated at 5×10$^4$ pfu/ml onto agar plates (LB bottom agar) and the plates were incubated overnight at 37° C. Filter membranes were overlaid onto plates for two minutes. Once removed, the filters were denatured, rinsed, dried and UV cross-linked. The filters were then incubated in pre-hyridization buffer (2× PIPES [pH 6.5], 5% formamide, 1% SDS and 100 µg/ml denatured salmon sperm DNA) for 2 h at 42° C. A 260 base-pair radiolabelled probe (SEQ ID NO: 3; $^{32}$P labelled by random priming) was added to the entire hybridization mix/filters, followed by hybridization for 18 hours at 42° C. The membranes were washed once at room temperature (10 min, 1×SSC, 0.1% SDS) and three times at 55° C. (15 min, 0.1×SSC, 0.1% SDS).

After they were washed, the membranes were analyzed by autoradiography as described above. Positive clones were plaque purified. The procedure was repeated with a second filter for four minutes to minimize spurious positives. Plaque-purified clones were rescued as lambda SK(−) phagemids. Cloned cDNAs were sequenced as described below.

EXAMPLE 11

Sequencing of Clones

Cloned cDNA inserts were sequenced by standard methods. Ausubel et al., *Current Protocols in Molecular Biology*, Wiley Interscience (1988). Briefly, appropriate concentrations of termination mixture, template and reaction mixture were subjected to an appropriate cycling protocol (95° C.,30s; 68° C.,30s; 72° C.,60s; ×25). Stop mixture was added to terminate the sequencing reactions. After heating at 92° C. for 3 minutes, the samples were loaded onto a denaturing 6% polyacrylamide sequencing gel (29:1 acrylamide:bis-acrylamide). Samples were electrophoresed for about 4 hours at 60 volts, constant current. After electrophoresis, the gels were dried in vacuo and autoradiographed.

The autoradiographs were analyzed manually. The resulting sequences were screened against the databases maintained by the National Center for Biotechnology Information (NIH, Bethesda, Md.; http://www.ncbi.nim.nih.govl) using the BLASTn program set with default parameters. Based on the sequence data, new sequencing primers were prepared and the process was repeated until the entire gene had been sequenced. All sequences were confirmed a minimum of three times in both orientations.

Nucleotide and amino acid sequences were also analyzed using the PCGENE software package (version 16.0). Per cent homology values for nucleotide sequences were calculated by the program NALIGN, using the following parameters: weight of non-matching nucleotides, 10; weight of non-matching gaps, 10; maximum number of nucleotides considered, 50; and minimum number of nucleotides considered, 50.

For amino acid sequences, per cent homology values were calculated using PALIGN. A value of 10 was selected for both the open gap cost and the unit gap cost.

EXAMPLE 12

Cloning of RLMP cDNA

The differential display PCR amplification products described in Example 9 contained a major band of approximately 260 base pairs. This sequence was used to screen a rat osteosarcoma (UMR 106) cDNA library. Positive clones were subjected to nested primer analysis to obtain the primer sequences necessary for amplifying the full length cDNA. (SEQ. ID NOs: 11, 12, 29, 30 and 31) One of those positive clones I selected for further study was designated clone 10-4.

Sequence analysis of the full-length cDNA in clone 10-4, determined by nested primer analysis, showed that clone 10-4 contained the original 260 base-pair fragment identified by differential display PCR. Clone 10-4 (1696 base pairs; SEQ ID NO: 2) contains an open reading frame of 1371 base pairs encoding a protein having 457 amino acids (SEQ ID NO: 1). The termination codon, TGA, occurs at nucleotides 1444-1446. The polyadenylation signal at nucleotides 1675-1680, and adjacent poly(A)$^+$ tail, was present in the 3' noncoding region. There were two potential N-glycosylation sites, Asn-Lys-Thr and Asn-Arg-Thr, at amino acid positions 113-116 and 257-259 in SEQ ID NO: 1, respectively. Two potential cAMP- and cGMP-dependent protein kinase phosphorylation sites, Ser and Thr, were found at amino acid positions 191 and 349, respectively. There were five potential protein kinase C phosphorylation sites, Ser or Thr, at amino acid positions 3, 115, 166, 219, 442. One potential ATP/GTP binding site motif A (P-loop), Gly-Gly-Ser-Asn-Asn-Gly-Lys-Thr, was determined at amino acid positions 272-279.

In addition, two highly conserved putative LIM domains were found at amino acid positions 341-391 and 400-451. The putative LIM domains in this newly identified rat cDNA clone showed considerable homology with the LIM domains of other known LIM proteins. However, the overall homology with other rat LIM proteins was less than 25%. RLMP (also designated 10-4) has 78.5% amino acid homology to the human enigma protein (see U.S. Pat. No. 5,504,192), but only 24.5% and 22.7% amino acid homology to its closest rat homologs, CLP-36 and RIT-18, respectively.

EXAMPLE 13

Northern Blot Analysis of RLMP Expression

Thirty µg of total RNA from ROBs, prepared according to Examples 1 and 2, was size fractionated by formaldehyde gel electrophoresis in 1% agarose flatbed gels and osmotically transblotted to nylon membranes. The blot was probed with a 600 base pair EcoR1 fragment of full-length 10-4 cDNA labeled with $^{32}$P-dCTP by random priming.

Northern blot analysis showed a 1.7 kb mRNA species that hybridized with the RLMP probe. RLMP mRNA was up-regulated approximately 3.7-fold in ROBs after 24 hours exposure to BMP-6. No up-regulation of RMLP expression was seen in BMP-2 or BMP4-stimulated ROBs at 24 hours.

EXAMPLE 14

Statistical Methods

For each reported nodule/osteocalcin result, data from 5-6 wells from a representative experiment were used to calculate the mean±S.E.M. Graphs may be shown with data normalized to the maximum value for each parameter to allow simultaneous graphing of nodule counts, mineralized areas and osteocalcin.

For each reported RT-PCR, RNase protection assay or Western blot analysis, data from triplicate samples of representative experiments, were used to determine the mean±S.E.M. Graphs may be shown normalized to either day 0 or negative controls and expressed as fold-increase above control values.

Statistical significance was evaluated using a one-way analysis of variance with post-hoc multiple comparison corrections of Bonferroni as appropriate. D. V. Huntsberger, "The Analysis of Variance," in *Elements of Statistical Variance*, P. Billingsley (ed.), pp. 298-330, Allyn & Bacon Inc., Boston, Mass. (1977) and Sigmastat, Jandel Scientific, Corte Madera, Calif. Alpha levels for significance were defined as p<0.05.

EXAMPLE 15

Detection of Rat LIM Mineralization Protein by Western Blot Analysis

Polyclonal antibodies were prepared according to the methods of England et al., *Biochim. Biophys. Acta*, 623:171 (1980) and Timmer et a., *J. Biol. Chem.*, 268:24863 (1993).

HeLa cells were transfected with pCMV2/RLMP. Protein was harvested from the transfected cells according to the method of Hair et al., *Leukemia Research*, 20:1 (1996). Western Blot Analysis of native RLMP was performed as described by Towbin et al., *Proc. Natl. Acad. Sci. USA*, 76:4350 (1979).

EXAMPLE 16

Synthesis of the Rat LMP-Unique (RLMPU)-Derived Human PCR Product

Based on the sequence of the rat LMP-1 cDNA, forward and reverse PCR primers (SEQ ID NOs: 15 and 16) were synthesized and a unique 223 base-pair sequence was PCR amplified from the rat LMP-1 cDNA. A similar PCR product was isolated from human MG63 osteosarcoma cell cDNA with the same PCR primers.

RNA was harvested from MG63 osteosarcoma cells grown in T-75 flasks. Culture supernatant was removed by aspiration and the flasks were overlayed with 3.0 ml of GIT solution per duplicate, swirled for 5-10 seconds, and the resulting solution was transferred to 1.5 ml eppendorf tubes (5 tubes with 0.6 ml/tube). RNA was purified by a slight modification of standard methods, for example, see Sambrook et al., Molecular Cloning: A Laboratory Manual, chapter 7, page 19, Cold Spring Harbor Laboratory Press (1989) and Boden 6t al., *Endocrinology*, 138:2820-28 (1997). Briefly, the 0.6 ml samples received 60 µl 2.0 M sodium acetate (pH 4.0), 550 µl water saturated phenol and 150 µl chloroform:isoamyl alcohol (49:1). After addiiton of those reagents, the samples were vortexed, centrifuged (10000×g; 20 min; 4 C) and the aqueous phase transferred to a fresh tube. Isopropanol (600 µl) was added and the RNA was precipitated overnight at −20° C. The samples were centrifuged (10000×g; 20 minutes) and the supernatant was aspirated gently. The pellets were resuspended in 400 µl of DEPC-treated water, extracted once with phenol-chloroform (1:1), extracted with chloroform:isoamyl alcohol (24:1) and precipitated overnight at −20° C. in 40 µl sodium acetate (3.0 M; pH 5.2) and 1.0 ml absolute ethanol; After precipitation, the samples were centrifuged (10000×g; 20 min), washed once with 70% ethanol, air dried for 5-10 minutes and resuspended in 20 µl of DEPC-treated water. RNA concentrations were derived from optical densities.

Total RNA (5 µg in 10.5 µl total volume in DEPC-H$_2$O) was heated at 65° C. for 5 minutes, and then added to tubes containing 4 µl 5× MMLV-RT buffer, 2 µl dNTPs, 2 µl dT17 primer (10 pmol/ml), 0.5 µl RNAsin (40 U/ml) and 1 µl MMLV-RT (200 units/µl). The reactions were incubated at 37° C. for 1 hour. Afterward, the MMLV-RT was inactivated by heating at 95° C. for 5 minutes. The samples were diluted by addition of 80 µL water.

Transcribed samples (5 µl) were subjected to polymerase-chain reaction using standard methodologies (50 µl total volume). Boden et al., *Endocrinology*, 138:2820-28 (1997); Ausubel et al., "Quantitation of rare DNAs by the polymerase chain reaction", in *Current Protocols in Molecular Biology*, chapter 15.31-1, Wiley & Sons, Trenton, N.J. (1990). Briefly, samples were added to tubes containing water and appropriate amounts of PCR buffer (25 mM MgCl$_2$, dNTPs, forward and reverse primers (for RLMPU; SEQ ID NOs: 15 and 16), $^{32}$P-dCTP, and DNA polymerase. Primers were designed to run consistently at 22 cycles for radioactive band detection and 33 cycles for amplification of PCR product for use as a screening probe (94° C., 30 sec, 58° C., 30 sec; 72° C., 20 sec).

Sequencing of the agarose gel-purified MG63 osteosarcoma-derived PCR product gave a sequence more than 95% homologous to the RLMPU PCR product. That sequence is designated HLMP unique region (HLMPU; SEQ ID NO: 6).

EXAMPLE 17

Screening of Reverse-Transcriptase-Derived MG63 cDNA

Screening was performed with PCR using specific primers (SEQ ID NOs: 16 and 17) as described in Example 7. A 717 base-pair MG63 PCR product was agarose gel purified and sequenced with the given primers (SEQ. ID NOs: 12, 15, 16, 17, 18, 27 and 28). Sequences were confirmed a minimum of two times in both directions. The MG63 sequences were aligned against each other and then against the full-length rat LMP cDNA sequence to obtain a partial human LMP cDNA sequence (SEQ ID NO: 7).

EXAMPLE 18

Screening of a Human Heart cDNA Library

Based on Northern blot experiments, it was determined that LMP-1 is expressed at different levels by several different tissues, including human heart muscle. A human heart cDNA library was therefore examined. The library was plated at 5×10⁴ pfu/ml onto agar plates (LB bottom agar) and plates were grown overnight at 37° C. Filter membranes were overlaid onto the plates for two minutes. Afterward, the filters denatured, rinsed, dried, UV cross-linked and incubated in pre-hyridization buffer (2× PIPES [pH 6.5]; 5% formamide, 1% SDS, 100 g/ml denatured salmon sperm DNA) for 2 h at 42° C. A radiolabelled, LMP-unique, 223 base-pair probe ($^{32}$P, random primer labelling; SEQ ID NO: 6) was added and hybridized for 18 h at 42° C. Following hybridization, the membranes were washed once at room temperature (10 min, 1×SSC, 0.1% SDS) and three times at 55° C. (15 min, 0.1× SSC, 0.1% SDS). Double-positive plaque-purified heart library clones, identified by autoradiography, were rescued as lambda phagemids according to the manufacturers' protocols (Stratagene, La Jolla, Calif.).

Restriction digests of positive clones yielded cDNA inserts of varying sizes. Inserts greater than 600 base-pairs in length were selected for initial screening by sequencing. Those inserts were sequenced by standard methods as described in Example 11.

One clone, number 7, was also subjected to automated sequence analysis using primers corresponding to SEQ ID NOs: 11-14, 16 and 27. The sequences obtained by these methods were routinely 97-100% homologous. Clone 7 (Partial Human LMP-1 cDNA from a heart library; SEQ. ID NO: 8) contained sequence that was more than 87% homologous to the rat LMP cDNA sequence in the translated region.

EXAMPLE 19

Determination of Full-Length Human LMP-1 cDNA

Overlapping regions of the MG63 human osteosarcoma cell cDNA sequence and the human heart cDNA clone 7 sequence were used to align those two sequences and derive a complete human cDNA sequence of 1644 base-pairs. NALIGN, a program in the PCGENE software package, was used to align the two sequences. The overlapping regions of the two sequences constituted approximately 360 base-pairs having complete homology except for a single nucleotide substitution at nucleotide 672 in the MG63 cDNA (SEQ ID NO: 7) with clone 7 having an "A" instead of a EGO at the corresponding nucleotide 516 (SEQ ID NO: 8).

The two aligned sequences were joined using SEQIN, another subprogram of PCGENE, using the "G" substitution of the MG63 osteosarcoma cDNA clone. The resulting sequence is shown in SEQ ID NO: 9. Alignment of the novel human-derived sequence with the rat LMP-1 cDNA was accomplished with NALIGN. The full-length human LMP-1 cDNA sequence (SEQ. ID NO: 9) is 87.3% homologous to the translated portion of rat LMP-1 cDNA sequence.

EXAMPLE 20

Determination of Amino Acid Sequence of Human LMP-1

The putative amino acid sequence of human LMP-1 was determined with the PCGENE subprogram TRANSL. The open reading frame in SEQ ID NO: 9 encodes a protein comprising 457 amino acids (SEQ. ID NO: 10). Using the PCGENE subprogram Palign, the human LMP-1 amino acid sequence was found to be 94.1% homologous to the rat LMP-1 amino acid sequence.

EXAMPLE 21

Determination of the 5 Prime Untranslated Region of the Human LMP cDNA

MG63 5' cDNA was amplified by nested RT-PCR of MG63 total RNA using a 5' rapid amplification of cDNA ends (5' RACE) protocol. This method included first strand cDNA synthesis using a lock-docking oligo (dT) primer with two degenerate nucleotide positions at the 3' end (Chenchik et al., *CLONTECHniques*. X:5 (1995); Borson et al., *PC Methods Applic.,* 2:144 (1993)). Second-strand synthesis is performed according to the method of Gubler et al., *Gene*. 25:263 (1983), with a cocktail of *Escherichia coli* DNA polymerase I, RNase H, and *E. coil* DNA ligase. After creation of blunt ends with T4 DNA polymerase, double-stranded cDNA was ligated to the fragment (5'-CTAATACGACTCACTAT-AGGGCTCGAGCGGCCGCCCGGGCAGGT-3') (SEQ.ID NO: 19). Prior to RACE, the adaptor-ligated cDNA was diluted to a concentration suitable for Marathon RACE reactions (1:50). Adaptor-ligated double-stranded cDNA was then ready to be specifically cloned.

First-round PCR was performed with the adaptor-specific oligonucleotide, 5'-CCATCCTAATACGACTCACTAT-AGGGC-3' (AP1) (SEQ.ID NO: 20) as sense primer and a Gene Specific Primer (GSP) from the unique region described in Example 16 (HLMPU). The second round of PCR was performed using a nested primers GSP1-HLMPU (antisense/reverse primer) (SEQ. ID NO: 23) and GSP2-HLMPUF (SEQ. ID NO: 24) (see Example 16; sense/forward primer). PCR was performed using a commercial kit (Advantage cDNA PCR core kit; CloneTech Laboratories Inc., Palo Alto, Calif.) that utilizes an antibody-mediated, but otherwise standard, hot-start protocol. PCR conditions for MG63 cDNA included an initial hot-start denaturation (94° C., 60 sec) followed by: 94° C., 30 sec; 60° C., 30 sec; 68° C., 4 min; 30 cycles. The first-round PCR product was approximately 750 base-pairs in length whereas the nested PCR product was approximately 230 base-pairs. The first-round PCR product was cloned into linearized pCR 2.1 vector (3.9 Kb). The inserts were sequenced in both directions using M13 Forward and Reverse primers (SEQ. ID NO: 11; SEQ. ID NO: 12)

19

EXAMPLE 22

Determination of Full-Length Human LMP-1 cDNA with 5 Prime UTR

Overlapping MG63 human osteosarcoma cell cDNA 5'-UTR sequence (SEQ ID NO: 21), MG63 717 base-pair sequence (Example 17; SEQ ID NO: 8) and human heart cDNA clone 7 sequence (Example 18) were aligned to derive a novel human cDNA sequence of 1704 base-pairs (SEQ.ID NO: 22). The alignment was accomplished with NALIGN, (both PCGENE and Omiga 1.0; Intelligenetics). Over-lapping sequences constituted nearly the entire 717 base-pair region (Example 17) with 100% homology. Joining of the aligned sequences was accomplished with SEQIN.

EXAMPLE 23

Construction of LIM Protein Expression Vector

The construction of pHIS-5ATG LMP-1s expression vector was carried out with the sequences described in Examples 17 and 18. The 717 base-pair clone (Example 17; SEQ ID NO: 7) was digested with ClaI and EcoRV. A small fragment (~250 base-pairs) was gel purified. Clone 7 (Example 18; SEQ ID NO: 8) was digested with ClaI and XbaI and a 1400 base-pair fragment was gel purified. The isolated 250 base-pair and 1400 base-pair restriction fragments were ligated to form a fragment of ~1650 base-pairs.

Due to the single nucleotide substitution in Clone 7 (relative to the 717 base-pair PCR sequence and the original rat sequence) a stop codon at translated base-pair 672 resulted. Because of this stop codon, a truncated (short) protein was encoded, hence the name LMP-1s. This was the construct used in the expression vector (SEQ ID NO: 32). The full length cDNA sequence with 5' UTR (SEQ ID NO: 33) was created by alignment of SEQ ID NO: 32 with the 5' RACE sequence (SEQ ID NO: 21). The amino acid sequence of LMP-1s (SEQ ID NO: 34) was then deduced as a 223 amino acid protein and confirmed by Western blot (as in Example 15) to run at the predicted molecular weight of ~23.7 kD.

The pHis-ATG vector (InVitrogen, Carlsbad, Calif.) was digested with EcoRV and XbaI. The vector was recovered and the 1650 base-pair restriction fragment was then ligated into the linearized pHis-ATG. The ligated product was cloned and amplified. The pHis-ATG-LMP-1s Expression vector, also designated pHIS-A with insert HLMP-1s, was purified by standard methods.

EXAMPLE 24

Induction of Bone Nodule Formation and Mineralization In Vitro with LMP Expression Vector Rat Calvarial cells were isolated and grown in secondary culture according to Example 1. Cultures were either unstimulated or stimulated with glucocorticoid (GC) as described in Example 1. A modification of the Superfect Reagent (Qiagen, Valencia, Calif.) transfection protocol was used to transfect 3 µg/well of each vector into secondary rat calvarial osteoblast cultures according to Example 25. Mineralized nodules were visualized by Von Kossa staining, as described in Example 3.

Human LMP-1s gene product overexpression alone induced bone nodule formation (~203 nodules/well) in vitro. Levels of nodules were approximately 50% of those induced by the GC positive control (~412 nodules/well). Other positive controls included the pHisA-LMP-Rat expression vector (~152 nodules/well) and the pCMV2/LMP-Rat-Fwd Expression vector (~206-nodules/well), whereas the negative controls included the pCMV2/LMP-Rat-Rev. Expression vector (~2 nodules/well) and untreated (NT) plates (~4 nodules/well). These data demonstrate that the human cDNA was at least as osteoinductive as the rat cDNA. The effect was less than that observed with GC stimulation, most likely due to suboptimal doses of Expression vector.

EXAMPLE 25

LMP-Induced Cell Differentiation In Vitro and In Vivo

The rat LMP cDNA in clone 10-4 (see Example 12) was excised from the vector by double-digesting the clone with NotI and ApaI overnight at 37° C. Vector pCMV2 MCS (InVitrogen, Carlsbad, Calif.) was digested with the same restriction enzymes. Both the linear cDNA fragment from clone 10-4 and pCMV2 were gel purified, extracted and ligated with T4 ligase. The ligated DNA was gel purified, extracted and used to transform *E. coli* JM109 cells for amplification. Positive agar-colonies were picked, digested with NotI and ApaI and the restriction digests were examined by gel electrophoresis. Stock cultures were prepared of positive clones.

A reverse vector was prepared in analogous fashion except that the restriction enzymes used were XbaI and HindIII. Because these restriction enzymes were used, the LMP cDNA fragment from clone 10-4 was inserted into pRc/CMV2 in the reverse (that is, non-translatable) orientation. The recombinant vector produced is designated pCMV2/RLMP.

An appropriate volume of pCMV10-4 (60 nM final conceritration is optimal [3 µg]; for this experiment a range of 0-600 nM/well [0-30 µg/well] final concentration is preferred) was resuspended in Minimal Eagle Media (MEM) to 450 µl final volume and vortexed for 10 seconds. Superfect was added (7.5 µl/ml final solution), the solution was vortexed for 10 seconds and then incubated at room termperature for 10 minutes. Following this incubation, MEM supplemented with 10% FBS (1 ml/well; 6 ml/plate) was added and mixed by pipetting.

The resulting solution was then promptly pipetted (1 ml/well) onto washed ROB cultures. The cultures were incubated for 2 hours at 37° C. in a humidified atmosphere containing 5% $CO_2$. Afterward, the cells were gently washed once with sterile PBS and the appropriate normal incubation medium was added.

Results demonstrated significant bone nodule formation in all rat cell cultures which were induced with pCMV10-4. For example, pCMV10-4 transfected cells produced 429 nodules/well. Positive control cultures, which were exposed to Trm, produced 460 nodules/well. In contrast, negative controls, which received no treatment, produced 1 nodule/well. Similarly, when cultures were transfected with pCMV10-4 (reverse), no nodules were observed.

For demonstrating de novo bone formation in vivo, marrow was aspirated from the hindlimbs of 4-5 week old normal rats (mu/+; heterozygous for recessive athymic condition). The aspirated marrow cells were washed in alpha MEM, centrifuged, and RBCs were lysed by resuspending the pellet in 0.83% $NH_4Cl$ in 10 mM Tris (pH 7.4). The remaining marrow cells were washed 3× with MEM and transfected for 2 hours with 9 µg of pCMV-LMP-1s (forward or reverse orientation)

per $3 \times 10^6$ cells. The transfected cells were then washed 2× with MEM and resuspended at a concentration of $3 \times 10^7$ cells/ml.

The cell suspension (100 µl) was applied via sterile pipette to a sterile 2×5 mm type I bovine collagen disc (Sulzer Orthopaedics, Wheat Ridge, Co.). The discs were surgically implanted subcutaneously on the skull, chest, abdomen or dorsal spine of 4-5 week old athymic rats (mu/mu). The animals were scarified at 3-4 weeks, at which time the discs or surgical areas were excised and fixed in 70% ethanol. The fixed specimens were analyzed by radiography and undecalcified histologic examination was performed on 5 µm thick sections stained with Goldner Trichrome. Experiments were also performed using devitalized (guanidine extracted) demineralized bone matrix (Osteotech, Shrewsbury, N.J.) in place of collagen discs.

Radiography revealed a high level of mineralized bone formation that conformed to the form of the original collagen disc containing LMP-is transfected marrow cells. No mineralized bone formation was observed in the negative control (cells transfected with a reverse-oriented version of the LMP-1s cDNA that did not code for a translated protein), and absorption of the carrier appeared to be well underway.

Histology revealed new bone trabeculae lined with osteoblasts in the LMP-1s transfected implants. No bone was seen along With partial resorption of the carrier in the negative controls.

Radiography of a further experiment in which 18 sets (9 negative control pCMV-LMP-REV & 9 experimental pCMV-LMP-1s) of implants were added to sites alternating between lumbar and thoracic spine in athymic rats demonstrated 0/9 negative control implants exhibiting bone formation (spine fusion) between vertebrae. All nine of the pCMV-LMP-1s treated implants exhibited solid bone fusions between vertebrae.

EXAMPLE 26

The Synthesis of pHIS-5' ATG LMP-1s Expression Vector from the Sequences Demonstrated in Examples 2 and 3.

The 717 base-pair clone (Example 17) was digested with ClaI and EcoRV (New England Biologicals, city, Mass.). A small fragment (~250 base-pairs) was gel purified. Clone No. 7 (Example 18) was digested with ClaI and XbaI. A 1400 base-pair fragment was gel purified from that digest. The isolated 250 base-pair and 1400 base-pair cDNA fragments were ligated by standard methods to form a fragment of ~1650 bp. The pHis-A vector (InVitrogen) was digested with EcoRV and XbaI. The linearized vector was recovered and ligated to the chimeric 1650 base-pair cDNA fragment. The ligated product was cloned and amplified by standard methods, and the pHis-A-5' ATG LMP-1s expression vector, also denominated as the vector pHis-A with insert HLMP-1s, was deposited at the ATCC as previously described.

EXAMPLE 27

The Induction of Bone Nodule Formation and Mineralization In Vitro With pHis-5' ATG LMP-1s Expression Vector Rat calvarial cells were isolated and grown in secondary culture according to Example 1. Cultures were either unstimulated or stimulated with glucocorticoid (GC) according to Example 1. The cultures were transfected with 3 µg of recombinant pHis-A vector DNA/well as described in Example 25. Mineralized nodules were visualized by Von Kossa staining according to Example 3.

Human LMP-1s gene product overexpression alone (i.e., without GC stimulation) induced significant bone nodule formation (~203 nodules/well) in vitro. This is approximately 50% of the amount of nodules produced by cells exposed to the GC positive control (~412 nodules/well). Similar results were obtained with cultures transfected with pHisA-LMP-Rat Expression vector (~152 nodules/well) and pCMV2/LMP-Rat-Fwd (~206 nodules/well). In contrast, the negative control pCMV2/LMP-Rat-Rev yielded (~2 nodules/well), while approximately 4 nodules/well were seen in the untreated plates. These data demonstrate that the human LMP-1 cDNA was at least as osteoinductive as the rat LMP-1 cDNA in this model system. The effect in this experiment was less than that observed with GC stimulation; but in some the effect was comparable.

EXAMPLE 28

LMP Induces Secretion of a Soluble Osteoinductive Factor

Overexpression of RLMP-1 or HLMP-1s in rat calvarial osteoblast cultures as described in Example 24 resulted in significantly greater nodule formation than was observed in the negative control. To study the mechanism of action of LIM mineralization protein conditioned medium was harvested at different time points, concentrated to 10×, sterile filtered, diluted to its original concentration in medium containing fresh serum, and applied for four days to untransfected cells.

Conditioned media harvested from cells transfected with RLMP-1 or HLMP-1s at day 4 was approximately as effective in inducing nodule formation as direct overexpression of RLMP-1 in transfected cells. Conditioned media from cells transfected with RLMP-1 or HLMP-1 in the reverse orientation had no apparent effect on nodule formation. Nor did conditioned media harvested from LMP-1 transfected cultures before day 4 induce nodule formation. These data suggest that expression of LMP-1 caused the synthesis and/or secretion of a soluble factor, which did not appear in culture medium in effectie amounts until 4 days post transfection.

Since overexpression of rLMP-1 resulted in the secretion of an osteoinductive factor into the medium, Western blot analysis was used to determine if LMP-1 protein was present in the medium. The presence of rLMP-1 protein was assessed using antibody specific for LMP-1 (QDPDEE) and detected by conventional means. LMP-1 protein was found only in the cell layer of the culture and not detected in the medium.

Partial purification of the osteoinductive soluble factor was accomplished by standard 25% and 100% ammonium sulfate cuts followed by DE-52 anion exchange batch chromatography (100 mM or 500 mM NaCl). All activity was observed in the high ammonium sulfate, high NaCl fractions. Such localization is consistent with the possibility of a single factor being responsible for conditioning the medium.

All cited publications are hereby incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

We claim:

1. An isolated nucleic acid molecule comprising a nucleotide sequence encoding an amino acid sequence comprising SEQ ID NO: 34 wherein the amino acid sequence exhibits bone mineralization activity when expressed in a host cell.

2. The isolated nucleic acid molecule of claim 1, wherein the amino acid sequence enhances bone formation when expressed in a host cell.

3. A vector comprising the isolated nucleic acid molecule of claim 1 or 2.

4. A host cell comprising the vector of claim 3, wherein the host cell is selected from the group consisting of prokaryotic cells, yeast cells, and mammalian cells.

5. The isolated nucleic acid molecule of claim 1 or 2, further comprising a label for detection.

6. A method of inducing bone formation comprising transfecting osteogenic precursor cells with an isolated nucleic acid molecule comprising a nucleotide sequence encoding an amino acid sequence comprising SEQ ID NO: 34 wherein the amino acid sequence exhibits bone mineralization activity when expressed in a host cell.

7. The method of claim 6, wherein the isolated nucleic acid molecule is in a vector.

8. The method of claim 7, wherein the vector is an expression vector.

9. The method of claim 8, wherein the vector is a plasmid.

10. The method of claim 8, wherein the vector is a virus.

11. The method of claim 10, wherein the virus is an adenovirus.

12. The method of claim 10, wherein the virus is a retrovirus.

13. The method of claim 6, wherein the osteogenic precursor cells are transfected ex vivo.

14. The method of claim 6, wherein the osteogenic precursor cells are transfected in vivo by direct injection of the isolated nucleic acid molecule.

15. The method of claim 6, wherein the LIM mineralization protein is HLMP-1 with a sequence comprising SEQ ID NO: 10.

16. The method of claim 6, wherein the LIM mineralization protein is HLMP-1s with a sequence consisting of SEQ ID NO: 34.

17. A method of fusing a spine, comprising:
(a) transfecting osteogenic precursor cells with an isolated nucleic acid molecule comprising a nucleotide sequence encoding an amino acid sequence comprising SEQ ID NO: 34 wherein the amino acid sequence exhibits bone mineralization activity when expressed in a host cell;
(b) admixing the transfected osteogenic precursor cells with a matrix; and
(c) contacting the matrix with the spine;
wherein expression of the nucleotide sequence encoding LIM mineralization protein causes mineralized bone formation in the matrix.

18. The method of claim 17, wherein the osteogenic precursor cells are transfected ex vivo.

19. The method of claim 17, wherein the LIM mineralization protein is selected from the group consisting of HLMP-1 with a sequence comprising SEQ ID NO: 10 and HLMP-1s with a sequence consisting of SEQ ID NO: 34.

20. A method of stimulating production of an osteogenic soluble factor by an osteogenic cell, comprising:
(a) transfecting the osteogenic cell with an isolated nucleic acid molecule comprising a nucleotide sequence encoding an amino acid sequence comprising SEQ ID NO: 34 wherein the amino acid sequence exhibits bone mineralization activity when expressed in a host cell; and
(b) overexpressing the isolated nucleic acid molecule.

21. The method of claim 14 wherein the isolated nucleic acid molecule is in a vector selected from the group consisting of a plasmid and a virus.

22. The method of claim 21, wherein the vector is a plasmid, which plasmid is directly injected into the muscle tissue.

* * * * *

UNITED STATES PATENT AND TRADEMARK OFFICE
CERTIFICATE OF CORRECTION

| | |
|---|---|
| PATENT NO. | : 7,825,228 B2 |
| APPLICATION NO. | : 10/951236 |
| DATED | : November 2, 2010 |
| INVENTOR(S) | : Hair et al. |

It is certified that error appears in the above-identified patent and that said Letters Patent is hereby corrected as shown below:

On the Face Page, in Field (73), under "Assignee", in Column 1, Line 1, after "University", insert -- (US) --.

In Column 1, Line 8, after "2001," delete "now U.S. Pat. No. 6,858,431,".

In Column 1, Line 54, delete "BMP4," and insert -- BMP-4, --, therefor.

In Column 1, Line 67, delete "et a.," and insert -- et al., --, therefor.

In Column 3, Line 59, delete "ascpect," and insert -- aspect, --, therefor.

In Column 6, Line 10, delete "lnterscience" and insert -- Interscience --, therefor.

In Column 6, Line 42, delete "occurrance" and insert -- occurrence --, therefor.

In Column 7, Line 25, delete "hybrization" and insert -- hybridization --, therefor.

In Column 7, Line 35, delete "hybrization" and insert -- hybridization --, therefor.

In Column 7, Line 52, delete "susbstantially" and insert -- substantially --, therefor.

In Column 7, Line 56, delete "inventon" and insert -- invention --, therefor.

In Column 8, Line 48, delete "initial i" and insert -- initial --, therefor.

In Column 9, Line 18, delete "hydridoma" and insert -- hybridoma --, therefor.

In Column 9, Line 47, delete "the-subject" and insert -- the subject --, therefor.

Signed and Sealed this
Twenty-ninth Day of March, 2011

David J. Kappos
*Director of the United States Patent and Trademark Office*

CERTIFICATE OF CORRECTION (continued)
U.S. Pat. No. 7,825,228 B2

In Column 9, Lines 50-51, delete "other-conventional" and insert -- other conventional --, therefor.

In Column 9, Line 64, delete "feasibiliity" and insert -- feasibility --, therefor.

In Column 12, Line 2, delete "Tithe" and insert -- the --, therefor.

In Column 13, Line 54, delete "pre-hyridization" and insert -- pre-hybridization --, therefor.

In Column 14, Line 7, delete "lnterscience" and insert -- Interscience --, therefor.

In Column 14, Line 20, delete "nih.govl)" and insert -- nih.gov/) --, therefor.

In Column 14, Line 50, delete "clones I" and insert -- clones --, therefor.

In Column 15, Line 27, delete "RMLP" and insert -- RLMP --, therefor.

In Column 15, Line 28, delete "BMP4-stimulated" and insert -- BMP-4-stimulated --, therefor.

In Column 15, Line 61, delete "et a.," and insert -- et al., --, therefor.

In Column 16, Line 4, delete "(RLMPU)-Derived" and insert -- (RLMPU) Derived --, therefor.

In Column 16, Line 22, delete "6t al.," and insert -- et al., --, therefor.

In Column 16, Line 27, delete "addiiton" and insert -- addition --, therefor.

In Column 16, Line 28, delete "4C)" and insert -- 4°C.) --, therefor.

In Column 16, Line 34, delete "phenol-chloroform" and insert -- phenol:chloroform --, therefor.

In Column 16, Line 34, delete "chloroform;isoamyl" and insert -- chloroform:isoamyl --, therefor.

In Column 16, Line 36, delete "ethanol;" and insert -- ethanol. --, therefor.

In Column 17, Line 31, delete "pre-hyridization" and insert -- pre-hybridization --, therefor.

In Column 18, Line 1, delete "EGO" and insert -- "G" --, therefor.

In Column 18, Line 40, delete "E. coil" and insert -- E. coli --, therefor.

In Column 18, Line 67, delete "12)" and insert -- 12). --, therefor.

In Column 20, Line 24, delete "agar-colonies" and insert -- agar colonies --, therefor.

In Column 20, Lines 36-37, delete "conceritration" and insert -- concentration --, therefor.

In Column 20, Line 42, delete "termperature" and insert -- temperature --, therefor.

In Column 20, Line 62, delete "(mu/+;" and insert -- (rnu/+; --, therefor.

In Column 21, Line 8, delete "(mu/mu)." and insert -- (rnu/rnu). --, therefor.

In Column 21, Line 19, delete "LMP-is" and insert -- LMP-ls --, therefor.

In Column 21, Lines 24-25, delete "osteroblasts" and insert -- osteoblasts --, therefor.

In Column 21, Line 26, delete "With" and insert -- with --, therefor.

In Column 22, Line 44, delete "effectie" and insert -- effective --, therefor.